(12) United States Patent
Gunasekaran et al.

(10) Patent No.: US 10,889,598 B2
(45) Date of Patent: Jan. 12, 2021

(54) METHOD TO MAKE SCALABLE ULTRATHIN HEXAGONALLY FACETED METAL-ORGANIC FRAMEWORK (MOF) AND METHOD OF USING SAME FOR DETECTING EXPLOSIVES AND OTHER NITRO-AROMATIC COMPOUNDS

(71) Applicant: Wisconsin Alumni Research Foundation, Madison, WI (US)

(72) Inventors: Sundaram Gunasekaran, Madison, WI (US); Anu Pratap Mylamparambil Udayan, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 16/193,451

(22) Filed: Nov. 16, 2018

(65) Prior Publication Data

US 2019/0152995 A1 May 23, 2019

Related U.S. Application Data

(60) Provisional application No. 62/589,127, filed on Nov. 21, 2017.

(51) Int. Cl.
*C07F 3/06* (2006.01)
*G01N 27/30* (2006.01)
(Continued)

(52) U.S. Cl.
CPC .............. *C07F 3/06* (2013.01); *C07F 3/003* (2013.01); *G01N 27/30* (2013.01); *G01N 27/4045* (2013.01); *G01N 27/48* (2013.01); *B01J 20/226* (2013.01); *B01J 20/3085* (2013.01); *G01N 33/0057* (2013.01); *G01N 33/227* (2013.01)

(58) Field of Classification Search
CPC .... G01N 27/30; G01N 27/4045; G01N 27/48; G01N 33/0057; G01N 33/227; G01N 33/20; B01J 20/226; B01J 20/3085; C07F 3/003; C07F 3/06; Y10T 436/145555; Y10T 436/147777; Y10T 436/17;
(Continued)

(56) References Cited

U.S. PATENT DOCUMENTS

| 2015/0191491 A1* | 7/2015 | Shieh | ..................... C07F 3/003 428/402 |
| 2017/0096394 A1* | 4/2017 | Eddaoudi | ............... B01J 20/226 |

(Continued)

FOREIGN PATENT DOCUMENTS

CN 105606672 * 5/2016

OTHER PUBLICATIONS

Yao et al. CrystEngComm, vol. 15, 2013, pp. 3601-3606.*
(Continued)

*Primary Examiner* — Maureen Wallenhorst
(74) *Attorney, Agent, or Firm* — Joseph T. Leone, Esq.; DeWitt LLP

(57) ABSTRACT

A method to make metal-organic frameworks (MOFs) in which a first aqueous solution of a transition metal salt is mixed with a second aqueous solution of an imidazole or alkyl-substituted imidazole to yield a product solution containing MOF crystals. The MOF crystals are used to fabricate electrodes for electrochemical detection of nitro-aromatic compounds.

14 Claims, 13 Drawing Sheets

(51) Int. Cl.

| | | |
|---|---|---|
| *G01N 27/404* | (2006.01) | |
| *G01N 27/48* | (2006.01) | |
| *G01N 33/22* | (2006.01) | |
| *C07F 3/00* | (2006.01) | |
| *B01J 20/30* | (2006.01) | |
| *G01N 33/00* | (2006.01) | |
| *B01J 20/22* | (2006.01) | |

(58) Field of Classification Search
CPC ......... Y10T 436/173076; Y10T 436/25; Y10T 436/25375
USPC ... 436/73, 81, 83, 84, 96, 98, 106, 110, 149, 436/150, 174, 177
See application file for complete search history.

(56) References Cited

U.S. PATENT DOCUMENTS

2018/0305379 A1* 10/2018 Wang .................... G01N 27/327
2018/0339284 A1* 11/2018 Yang ........................ C02F 1/285

OTHER PUBLICATIONS

Pan et al. Chemical Communications, vol. 47, 2011, pp. 2071-2073.*
Jian et al. RSC Advances, vol. 5, 2015, pp. 48433-48441.*
Watanabe et al. Advanced Powder Technology, vol. 28, Sep. 18, 2017, pp. 3104-3110.*
Prathap et al. Advanced Sustainable Systems, vol. 2, Jul. 24, 2018, pp. 180053 (1-9).*
Alizadeh, T. Preparation of Magnetic TNT-Imprinted Polymer Nanoparticles and Their Accumulation onto Magnetic Carbon Paste Electrode for TNT Determination. *Biosens. Bioelectron.* 2014, 61, 532-540.
Anu Prathap et al., Polyaniline-Based Highly Sensitive Microbial Biosensor for Selective Detection of Lindane. *Anal. Chem.* 2012, 84 (15), 6672-6678.
Anu Prathap et al., Synthesis of NiCo2O4 and Its Application in the Electrocatalytic Oxidation of Methanol. *Nano Energy* 2013, 2 (5), 1046-1053.
Anu Prathap et al., Simultaneous Detection of Guanine, Adenine, Thymine, and Cytosine at polyaniline/MnO2 Modified Electrode. *Electrochim. Acta* 2013, 114, 285-295.
Anu Prathap et al., A New Insight into Electrochemical Detection of Eugenol by Hierarchical Sheaf-like Mesoporous NiCo2O4. *Nano Res.* 2015, 8 (8), 2636-2645.
Arjmandi, et al., Measuring the Electric Charge and Zeta Potential of Nanometer-Sized Objects Using Pyramidal-Shaped Nanopores. *Anal. Chem.* 2012, 84 (20), 8490-8496.
Bétard et al., Metal-Organic Framework Thin Films: From Fundamentals to Applications. *Chemical Reviews.* 2012, pp. 1055-1083.
Chaikittisilp et al., Nanoporous Carbons through Direct Carbonization of a Zeolitic Imidazolate Framework for Supercapacitor Electrodes. *Chem. Commun.* 2012, 48 (58), 7259.
Chen et al., Poly[meso-tetrakis(2-Thienyl)porphyrin] for the Sensitive Electrochemical Detection of Explosives. *Sensors Actuators, B Chem.* 2010, 147 (1), 191-197.
Chen, et al., Determination of Explosives Using Electrochemically Reduced Graphene. *Chem.—An Asian J.* 2011, 6 (5), 1210-1216.
Chen et al., Enhanced Electrocatalytic Activity of Nitrogen-Doped Graphene for the Reduction of Nitro Explosives. *Electrochem. commun.* 2012, 16 (1), 30-33.
Chevallier et al., Metalloporphyrin-Functionalised Diamond Nano-Particles as Sensitive Layer for Nitroaromatic Vapours Detection at Room-Temperature. *Sensors Actuators, B Chem.* 2010, 151 (1), 191-197.
Cortada et al., Determination of Nitroaromatic Explosives in Water Samples by Direct Ultrasound-Assisted Dispersive Liquid-Liquid Microextraction Followed by Gas Chromatography-Mass Spectrometry. *Talanta* 2011, 85 (5), 2546-2552.

Fierke et al., Receptor-Based Detection of 2,4-Dinitrotoluene Using Modified Three-Dimensionally Ordered Macroporous Carbon Electrodes. *ACS Appl. Mater. Interfaces* 2012, 4 (9), 4731-4739.
Furukawa et al., The Chemistry and Applications of Metal-Organic Frameworks. *Science* 2010, 9 (6149), 1230444.
Gao et al., Polymer-metal-organic Framework Core-shell Framework Nanofibers via Electrospinning and Their Gas Adsorption Activities. *RSC Adv.* 2016, 6 (9), 7078-7085.
Goh et al., Graphene-Based Electrochemical Sensor for Detection of 2,4,6-Trinitrotoluene (TNT) in Seawater: The Comparison of Single-, Few-, and Multilayer Graphene Nanoribbons and Graphite Microparticles. *Anal. Bioanal. Chem.* 2011, 399 (1), 127-131.
Gross et al., Aqueous Room Temperature Synthesis of Cobalt and Zinc Sodalite Zeolitic Imidizolate Frameworks. *Dalt. Trans.* 2012, 41 (18), 5458.
He et al., Facile Synthesis of Zeolitic Imidazolate Framework-8 from a Concentrated Aqueous Solution. *Microporous Mesoporous Mater.* 2014, 184, 55-60.
Jamil et al., Rapid Detection of TNT in Aqueous Media by Selective Label Free Surface Enhanced Raman Spectroscopy. *Talanta* 2015, 134, 732-738.
Lee et al., Metal-Organic Framework Materials as Catalysts. *Chem. Soc. Rev.* 2009, 38 (5), 1450-1459.
Li et al., Selective Gas Adsorption and Separation in Metal-organic Frameworks. *Chem. Soc. Rev.* 2009, 38 (5), 1477.
Liang et al., Composites of Polyaniline Nanofibers and Molecularly Imprinted Polymers for Recognition of Nitroaromatic Compounds. *Chem.—A Eur. J.* 2011, 17 (21), 5989-5997.
Lu et al., Determination of Explosives Based on Novel Type of Sensor Using Porphyrin Functionalized Carbon Nanotubes. *Colloids Surfaces B Biointerfaces* 2011, 88 (1), 396-401.
Mirasoli et al., Development of a Chemiluminescence-Based Quantitative Lateral Flow Immunoassay for on-Field Detection of 2,4,6-Trinitrotoluene. *Anal. Chim. Acta* 2012, 721, 167-172.
Nie et al., Two-Dimensional Molecular Imprinting Approach for the Electrochemical Detection of Trinitrotoluene. *Sensors Actuators, B Chem.* 2011, 156 (1), 43-49.
Pesavento et al., Voltammetric Platform for Detection of 2,4,6-Trinitrotoluene Based on a Molecularly Imprinted Polymer. *Anal. Bioanal. Chem.* 2013, 405 (11), 3559-3570.
Prathap, A Novel Non-Enzymatic Lindane Sensor Based on CuO-MnO2 Hierarchical Nano-Microstructures for Enhanced Sensitivity. *Chem. Commun.* 2015, 51, 4376-4379.
Qu et al., Electrochemical Sensor Prepared from Molecularly Imprinted Polymer for Recognition of 1,3-Dinitrobenzene (DNB). *Chinese J. Chem.* 2009, 27 (10), 2043-2048.
Qu et al., Resonance Energy Transfer-Based Nanospectroscopy for Sensitive and Selective Detection of 2,4,6-Trinitrotoluene (TNT). *Chem. Commun.* 2011, 47 (4), 1237-1239.
Ren et al., Polyacrylic Acid@zeolitic Imidazolate Framework-8 Nanoparticles with Ultrahigh Drug Loading Capability for pH-Sensitive Drug Release. *Chem. Commun.* 2014, 50 (8), 1000-1002.
Romolo et al., Field Detection Capability of Immunochemical Assays during Criminal Investigations Involving the Use of TNT. *Forensic Sci. Int.* 2015, 246, 25-30.
Rouquerol et al., Adsorption by Powders and Porous Solids: Principles, Methodology and Applications: Second Edition; 2013 (Book—Table of Contents Provided).
Rosi et al., Hydrogen Storage in Microporous Metal-Organic Frameworks. *Science* 2003, 300 (5622), 1127-1129.
Salinas et al., Fluorogenic Detection of Tetryl and TNT Explosives Using Nanoscopic-Capped Mesoporous Hybrid Materials. *J. Mater. Chem. A* 2013, 1 (11), 3561.
Seenivasan et al., An Electrochemical Immunosensing Method for Detecting Melanoma Cells. *Biosens. Bioelectron.* 2015, 68, 508-515.
Seenivasan et al., Highly Sensitive Detection and Removal of Lead Ions in Water Using Cysteine-Functionalized Graphene Oxide/Polypyrrole Nanocomposite Film Electrode. *ACS Appl. Mater. Interfaces* 2015, 7 (29), 15935-15943.

(56) References Cited

OTHER PUBLICATIONS

Seenivasan et al., Microfluidic-Integrated Patterned ITO Immunosensor for Rapid Detection of Prostate-Specific Membrane Antigen Biomarker in Prostate Cancer. *Biosens. Bioelectron.* 2017, 95, 160-167.

Senesac et al., Nanosensors for Trace Explosive Detection. *Materials Today.* 2008, pp. 28-36.

Shi et al., {MSU/PDDA}n LBL Assembled Modified Sensor for Electrochemical Detection of Ultratrace Explosive Nitroaromatic Compounds. *Electrochem. commun.* 2007, 9 (7), 1719-1724.

Shi et al., Electrochemical Sensor Prepared from Molecularly Imprinted Polymer for Recognition of TNT. *Polym. Compos.* 2015, 36 (7), 1280-1285.

Stringer et al., Detection of Nitroaromatic Explosives Using a Fluorescent-Labeled Imprinted Polymer. *Anal. Chem.* 2010, 82 (10), 4015-4019.

Tu et al., Room Temperature Syntheses of Zeolitic-Imidazolate Framework (ZIF) Nanocrystals. *Chem. Commun.* 2014, 50 (87), 13258-13260.

Üzer et al., Selective Colorimetric Determination of TNT Partitioned between an Alkaline Solution and a Strongly Basic Dowex 1-X8 Anion Exchanger. *Forensic Sci. Int.* 2008, 174 (2-3), 239-243.

Wilson et al., Electrochemiluminescence Enzyme Immunoassays for TNT and Pentaerythritol Tetranitrate. *Anal. Chem.* 2003, 75 (16), 4244-4249.

Xia et al., Turn-on and near-Infrared Fluorescent Sensing for 2,4,6-Trinitrotoluene Based on Hybrid (Gold Nanorod)-(Quantum Dots) Assembly. *Anal. Chem.* 2011, 83 (4), 1401-1407.

Yaghi et al., Selective Guest Binding by Tailored Channels in a 3-D Porous zinc(II)-Benzenetricarboxylate Network. *J. Am. Chem. Soc.* 1997, 119 (12), 2861-2868.

Yan et al., Highly Ordered Binary Assembly of Silica Mesochannels and Surfactant Micelles for Extraction and Electrochemical Analysis of Trace Nitroaromatic Explosives and Pesticides. *Anal. Chem.* 2015, 87 (8), 4436-4441.

Yang et al., Make It Different: The Plasma Treated Multi-Walled Carbon Nanotubes Improve Electrochemical Performances toward Nitroaromatic Compounds. *Electrochim. Acta* 2012, 76, 354-362.

Zang et al., Electrochemical Detection of Ultratrace Nitroaromatic Explosives Using Ordered Mesoporous Carbon. *Anal. Chim. Acta* 2011, 683 (2), 187-191.

Zhang et al., Electrochemical Sensor for Detecting Ultratrace Nitroaromatic Compounds Using Mesoporous SiO2-Modified Electrode. *Anal. Chem.* 2006, 78 (6), 1967-1971.

\* cited by examiner

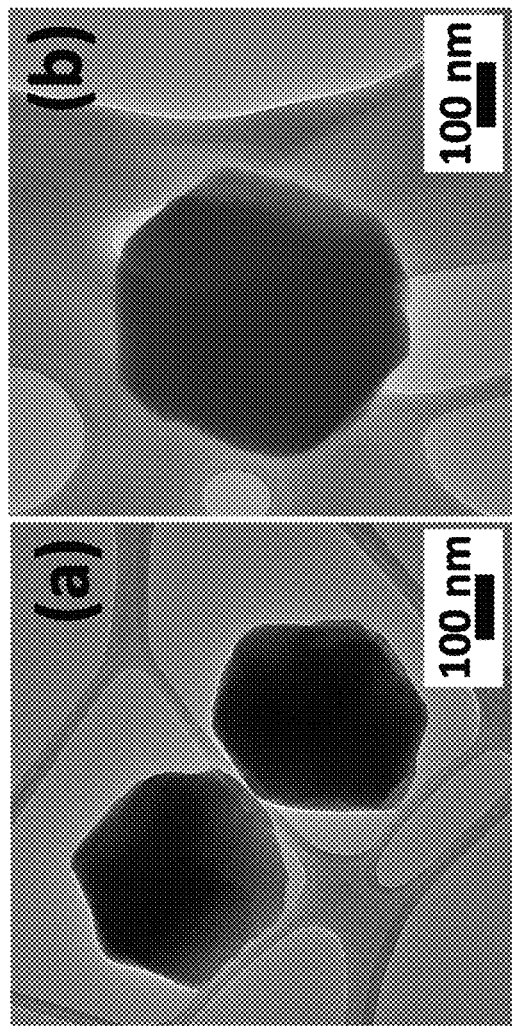
FIG. 2A
FIG. 2B
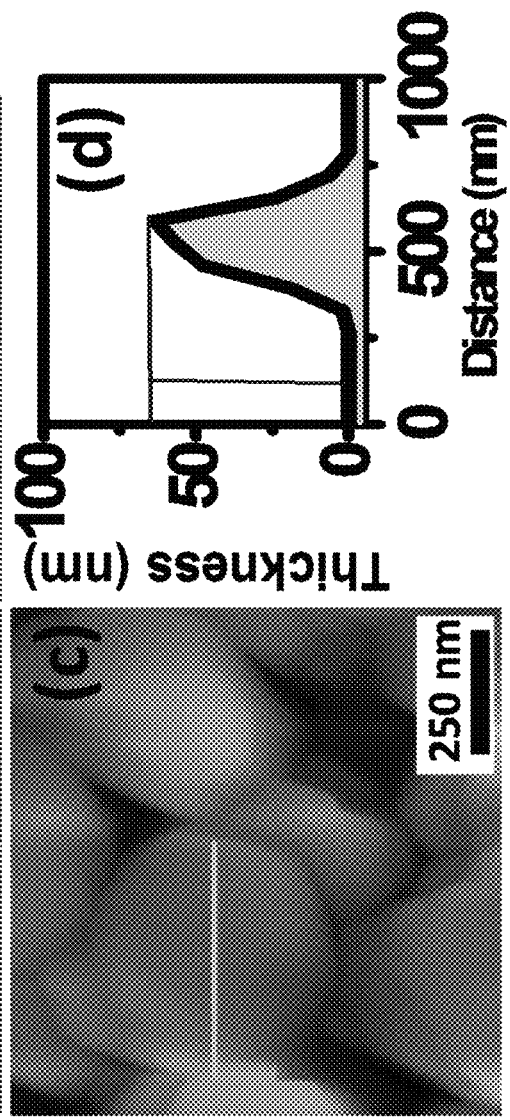
FIG. 2C
FIG. 2D

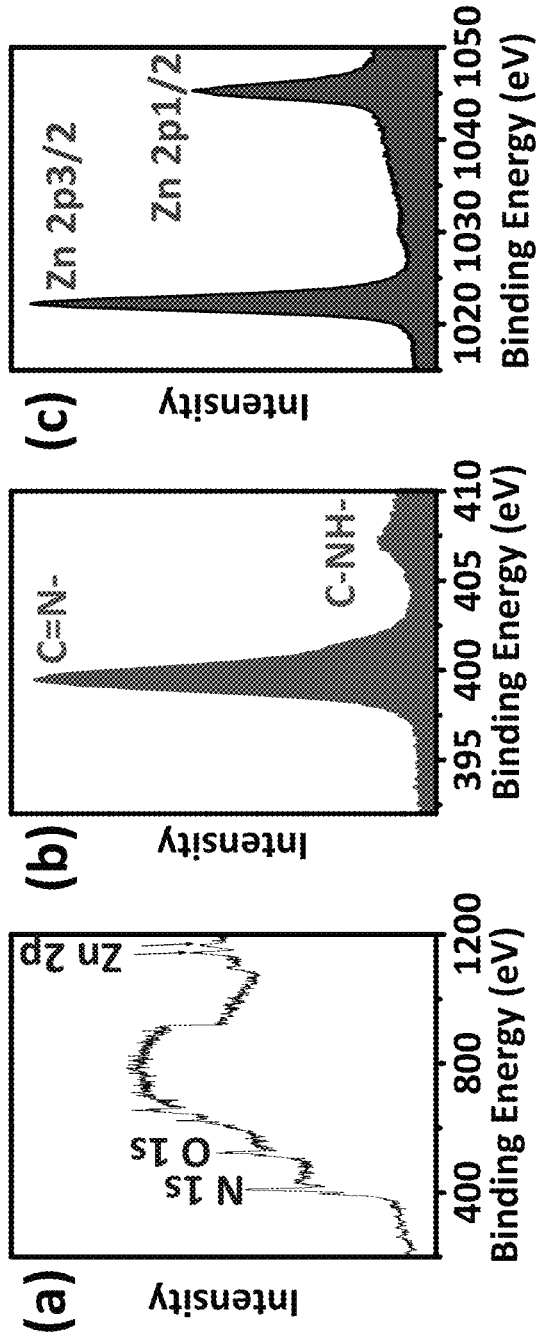
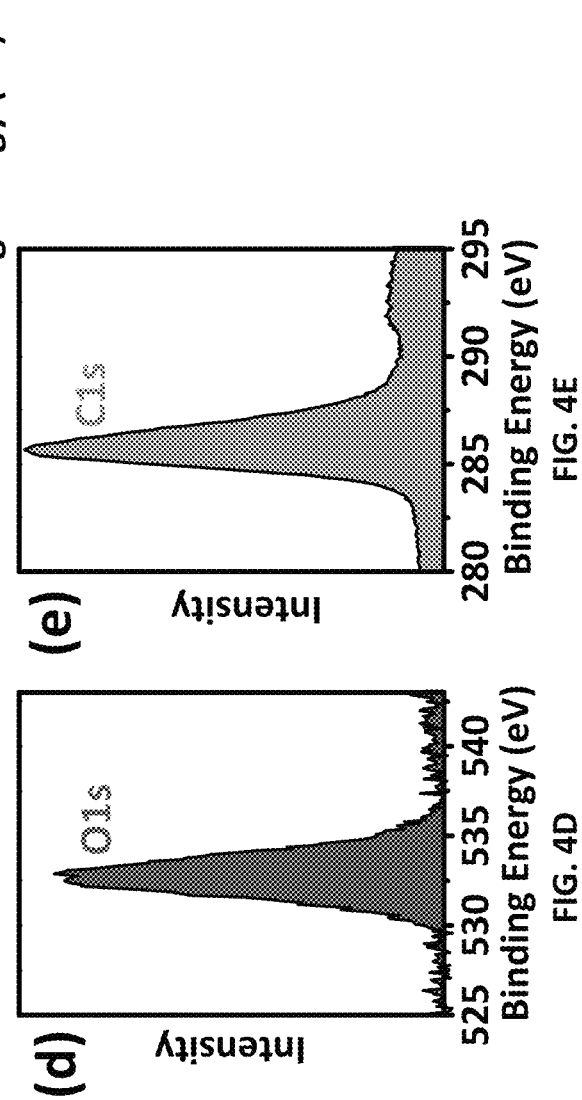
FIG. 4A
FIG. 4B
FIG. 4C
FIG. 4D
FIG. 4E

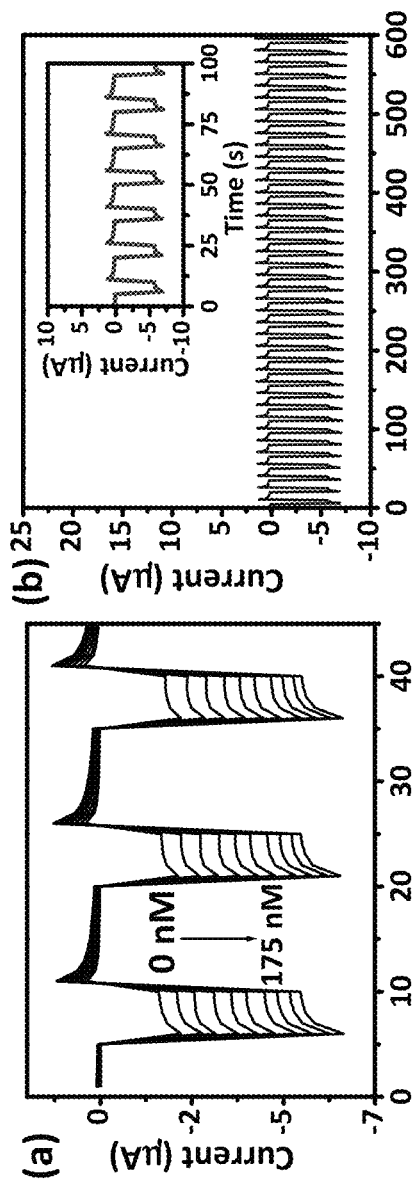
FIG. 5A
FIG. 5B
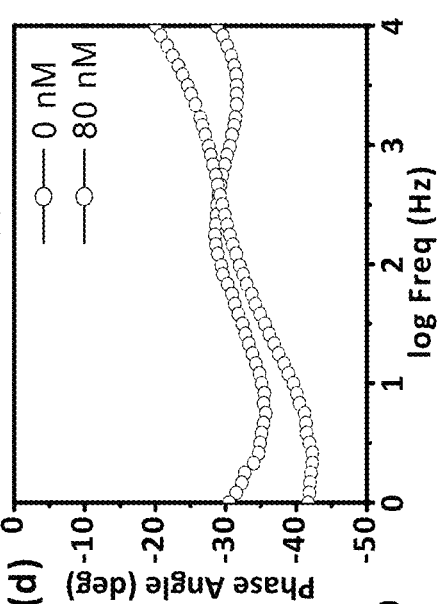
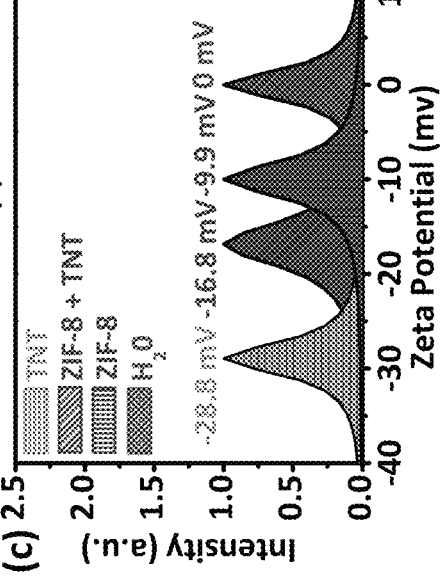
FIG. 5C
FIG. 5D

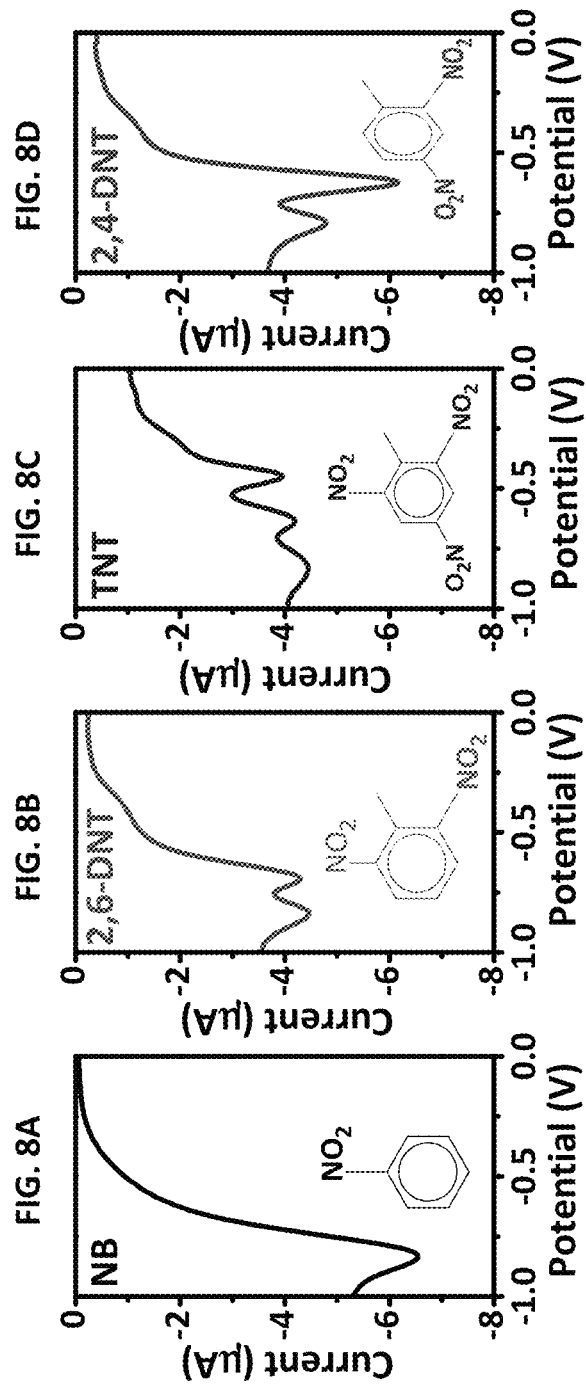

METHOD TO MAKE SCALABLE ULTRATHIN HEXAGONALLY FACETED METAL-ORGANIC FRAMEWORK (MOF) AND METHOD OF USING SAME FOR DETECTING EXPLOSIVES AND OTHER NITRO-AROMATIC COMPOUNDS

CROSS-REFERENCE TO RELATED APPLICATIONS

Priority is hereby claimed to provisional application Ser. No. 62/589,127, filed Nov. 21, 2017, which is incorporated herein.

FEDERAL FUNDING STATEMENT

This invention was made with government support under 17-CRHF-0-6055 awarded by the USDA/NIFA. The government has certain rights in the invention.

BACKGROUND

Modern organometallic chemistry emerged from the work of Alfred Werner, the 1913 Nobel Prize winner in chemistry. It was Werner who first investigated the interactions of organic and inorganic ligands with metal centers, proposed the octahedral configuration of transition metal complexes, and thus developed the basis for modern coordination chemistry.[1]

In the intervening decades, a host of organometallic materials have been fabricated and characterized. Among these organometallic materials are zeolitic imidazole frameworks (ZIFs), a type of metal-organic frameworks (MOFs). ZIFs are micro- or nanoporous crystalline coordination polymers constructed by bridging tetrahedral metal ions with organic ligands.[2] For the past two decades, ZIFs have attracted the interest of many researchers in a vast array of application, including in catalysis, nanotechnology devices, biomedicine, energy technologies, gas storage, chemical sensing, and drug delivery.[3-6] Particular attention has been drawn to the zinc 2-methylimidazolate known as ZIF-8, $Zn(C_4H_5N_2)_2$, sometimes trivially designated $Zn(MeIm)_2$. ZIF-8 is commercially sold by several international suppliers, including BASF, Ludwigschafen, Germany (under the unregistered trademark Basolite Z1200).[2]

The conventional route used to prepare ZIF-8 materials uses a large amount of organic solvent (DMF or methanol) and requires long reaction times.[3-6] The procedure is complicated and produces large amounts of by-products.[7] Recently, considerable efforts have been devoted to realizing alternative routes to making ZIF-8, routes that are more environmentally friend (i.e., "green") and less complicated. For example, Gross et al describe a method to prepare ZIF-8 in aqueous medium at room temperature.[8] ZIFs can also be obtained in the presence of other additives such as triblock copolymers, ammonium hydroxide and PVP in aqueous solvent systems.[3-6] However, the micropore volume of the resulting ZIFs (roughly 0.30 $cm^3/g$) was smaller than what is generally considered an ideal micropore volume (roughly 0.663 $cm^3/g$). This makes these prior art methods inefficient.[8] Thus, there remains a long-felt and unmet need for a method to synthesize ZIF-8 nano-structures that is simple and environmentally friendly.

The recent rise in global terrorism has stimulated the necessity of sensitive and low-cost sensing devices to ferret out explosive material.[9-11] Nitroaromatic compounds such as trinitrotoluene (TNT), dinitrotoluene (DNT), 1,3,5-trinitro-1,3,5-triazinane (RDX) and dinitrobenzene (DNB) are the primary components used to prepare the most widely employed commercial and military explosives.[12,13] In addition to their explosiveness, nitroaromatic compounds, as well as the products formed upon their detonation, are also toxic to humans and persistent environmental pollutants.[12, 13] Spills from chemical munitions and military-training sites into groundwater and/or seawater also pose a threat to human health and to the environment.[12,13] Notably, the United States Environmental Protection Agency has determined that TNT is a human carcinogen based on animal studies.[12,13] Therefore, it is very desirable to have a fast, easy, sensitive, robust, and inexpensive analytical method for detecting nitroaromatic-based explosives.

Traditional detection methods for TNT residue include surface-enhanced raman scattering, high-performance liquid chromatography, terahertz spectroscopy, ion mobility spectrometry, X-ray dispersion, and immunoassay techniques.[12,13] These instrumental techniques are highly selective and sensitive, but are quite expensive, tedious, and not easily portable.[12,13] Also, these methods are slow, their detection limit is less-than-ideal, and special pre-treatments are required before analysis.[12,13] Among the instrumental methods, an electrochemical approach theoretically offers rapid detection, with high precision, real-time detection.[14-20] However, the voltammertric response of conventional electrodes in response to TNT shows poor electrochemical activity, selectivity and electrode poisoning. Additionally, explosives such as DNT, which have a decreased number of nitro groups, are more resistant to electrochemical reduction, making the electrochemical detection approach even more problematic.[14-20] In short, nitroaromatic explosives present a host of distinct and wide-ranging public safety risks. These same explosives, however, are ubiquitous in all of the militaries around the globe and are widely used in commercial excavation, mining, and demolition work. Preventing their improper proliferation has historically proven difficult. Therefore; a simple electrochemical method for sensitive and selective detection of nitroaromatic explosives is highly desirable.

SUMMARY

Disclosed herein is a simple colloidal chemistry method for making a highly porous zeolite synthesis typically took two minutes compared to hours and days in non-aqueous conditions. The prepared ZIF-8 was then studied as an electrochemical sensing material for the detection of nitroaromatic explosive 2,4,6-trinitrotoluene (TNT), in aqueous phase and gas phase. This work for the first time explores the detailed kinetics for the electrochemical reduction of nitroaromatic explosive. We demonstrate a linear range from 1 nM to 460 nM in pulse voltammetric mode for the determination of 2,4,6-trinitrotoluene in aqueous media. We achieved a detection limit of 346 pM. Further, it has been shown that the sensor can detect other nitroaromatic explosives such as 2,4-dinitrotoluene (2,4-DNT), 2,6-dinitrotoluene (2,6-DNT), and nitrobenzene (NB). Moreover, ZIF-8 modified electrode showed excellent anti-interference property. Zeta potential study further proved that TNT molecule adsorbs onto the ZIF-8 surfaces. Based on the work, an electrochemical reaction mechanism for TNT reduction was also proposed. The applicability of ZIF-8 modified electrode was also demonstrated in the gas phase, showing the feasibility for on-site explosive detection.

Thus, disclosed herein is a method to make metal-organic frameworks (MOFs). The method comprises mixing a first aqueous solution comprising a transition metal salt with a second aqueous solution comprising imidazole or alkyl-substituted imidazole for a time and at a temperature to yield a product solution containing MOF crystals. The transition metal salt is preferably a metal selected from the group consisting of scandium, titanium, vanadium, chromium, manganese, iron, cobalt, nickel, copper, and zinc, and an anion selected from the group consisting of nitrate, sulfate, acetate, and halide. The preferred MOF is a ZIF comprising zinc or cobalt atoms linked through nitrogen atoms by ditopic imidazolate moieties. This provides for tunable, nano-sized pores formed by four-, six-, eight-, and/or twelve-membered ring $ZnN_4$, and $CoN_4$ tetrahedras. Preferred anions are nitrate or acetate.

The first aqueous solution may comprise from about 0.01 M to about 0.5 M of the transition metal salt and the second aqueous solution may comprise from about 1 mM to about 100 mM of the imidazole or alkyl-substituted imidazole. In the most preferred method, the first aqueous solution comprises zinc nitrate and the second aqueous solution comprises 2-methylimidazole. The synthesis solution described in the examples had a molar (M) ratio of 2-methylimidazole: $Zn^{2+}:H_2O$ of 1:2.4:19.8.

The first aqueous solution and the second aqueous solution may be mixed for a time of from about 1 minute to about 10 minutes to yield the production solution. The two solutions may be mixed at a temperature of from about 20±5° C. (about 293.15 K±5K).

The MOF crystals may be separated from the product solution by any means now known or developed in the future, including but not limited to centrifugation, filtration, precipitation, and the like. The separated crystals may be dried by any means now known or developed in the future. Air drying at a temperature of from about 40° C. to about 100° C. (about 313.15 K to about 473.15 K) is preferred.

Also disclosed herein is a composition of matter comprising a MOF disposed on an electrode substrate. The MOF may be fabricated by the method disclosed herein.

Also disclosed herein is a method of detecting nitro-aromatic compounds. The method comprises:

(a) contacting a solution or a gas suspected of containing a nitro-aromatic compound with an electrode of an electrochemical cell, wherein the electrode comprises a MOF disposed on a surface of the electrode;

(b) applying a first electric potential (voltage) to the electrode within the electrochemical cell and measuring current (amperage) generated in the electrochemical cell in response to the applied potential;

(c) comparing the current generated in step (b) with a standard curve of current data generated using the electrochemical cell of step (a) and standard solutions or gases containing known concentrations of at least one nitro-aromatic compound.

The MOF used in the method is preferably ZIF-8. The MOF may be fabricated as recited herein.

The method to make the MOF is a simple, novel green approach. By using ZIF-8 a new electrochemical sensor was demonstrated for selective sensing of nitro-aromatic explosives, including TNT and RDX. The sensor measures the electrochemical current from the reduction of the nitroaromatic compounds. We demonstrate a linear range for the determination of TNT up to 460 nM in aqueous phase. Further, it has been shown that the sensor can detect other nitroaromatic explosives with high sensitivity. This study also demonstrates electrochemical sensing of TNT vapors at laboratory scale.

BRIEF DESCRIPTION OF THE DRAWINGS

FIG. 1A is an X-ray powder diffractogram of the ZIF-8. FIG. 1B depicts nitrogen adsorption-desorption isotherms; Inset: BJH pore size curves. FIG. 1C is the FTIR spectrum of the ZIF-8. FIG. 1D shows the thermogram of the ZIF-8 and the corresponding derivative curve.

FIGS. 2A, 2B, 2C, and 2D. Morphology of ZIF-8 made according to the disclosed method. FIGS. 2A and 2B are high-resolution transmission electron microscopic (HR-TEM) images of the ZIF-8. FIG. 2C is a tapping mode atomic force microscopic (AFM) topographic image. FIG. 2D is a height profile corresponding to the AFM image shown in FIG. 2C.

FIGS. 4A through 4E are X-ray photoelectron spectroscopy (XPS) spectra for ZIF-8 made according to the present method. FIG. 4A is a high-resolution XPS spectrum for the ZIF-8. FIG. 4B is the XPS spectrum for N 1s. FIG. 4C is the XPS spectrum for Zn 2p. FIG. 4D is the XPS spectrum for O 1s. FIG. 4E is the XPS spectrum for C 1s.

FIG. 5A depicts pulsed amperometric response (n=3) of the ZIF-8-modified electrode to different concentrations of TNT (E1=0 V for 5 s; E2=−0.8 V for 5 s and E3=0 V, for 5 s). FIG. 5B depicts pulsed amperometric response (n=50) of the ZIF-8-modified electrode to 50 nM of TNT. The inset shows an enlarged view. FIG. 5C depicts zeta potential measurements of ZIF-8 aqueous solution, TNT solution (50 nM), $H_2O$, and ZIF-8 aqueous solution with 50 nM TNT. FIG. 5D is Bode plot for the electrode recorded in the frequency range of 0.1 Hz to 10 kHz, using a sinusoidal potential perturbation with an amplitude of 5 mV in 0.5 M KCl solution in the absence and presence of 80 nM TNT.

FIGS. 8A through 8D show DPV plots of nitrobenzene (NB) (FIG. 8A), 2,6-dinitrotoluene (2,6-DNT) (FIG. 8B), 2,4-dinitrotoluene (2,4-DNT) (FIG. 8C), and trinitrotoluene (TNT) (FIG. 8D) at the ZIF-8-modified electrode. DPV parameters: peak width=0.2 s; Pulse period=0.5 s; increment=10 mV.

DETAILED DESCRIPTION

Abbreviations and Definitions

Figure 1A:
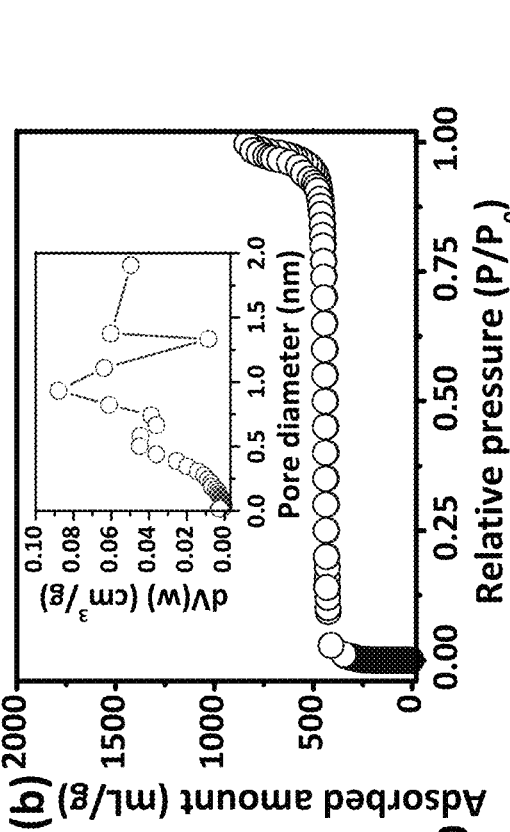
FIGS. 1A, 1B, 1C, and 1D. Characterization of ZIF-8 made according to the disclosed method.

AFM=atomic force microscopy. BET=Brunauer-Emmett-Teller surface area calculated according to ISO 9277 "Determination of the specific surface area of solids by gas adsorption—BET method." CV=cyclic voltammetry. DNB=dinitrobenzene. DNT=dinitrotoluene. 2,4-DNT=2,4-dinitrotoluene. 2,6-DNT=2,6-dinitrotoluene. DPV=differential pulse voltammetry. DMF=dimethyl formamide. HRTEM=high-resolution transmission electron microscopy. MOF=metal-organic framework. NB=nitrobenzene. PVP=polyvinylpyrrodlidone. RDX=1,3,5-trinitro-1,3,5-triazinane. SPE=screen printed electrode. TNT=trinitrotoluene. TEM=transmission electron microscopy. XPS=X-ray photoelectron spectroscopy. XRD=X-ray diffraction spectroscopy. ZIF=zeolitic imidazole framework.

The word "solution" as used herein is given a broader definition to include true solutions in which a solute is solvated by a solvent, as well as suspensions, dispersions, colloids, aerosols, and the like.

"Transition metal" means any element in the d-block of the periodic table, that is, any element within Groups 3 to 12 on the periodic table. The term explicitly includes, but is not limited to scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, and gold.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more," unless explicitly defined to the contrary.

All combinations of method or process steps as used herein can be performed in any order, unless otherwise specified or clearly implied to the contrary by the context in which the referenced combination is made.

The methods disclosed herein can comprise, consist of, or consist essentially of the essential elements and limitations of the method described, as well as any additional or optional ingredients, components, or limitations described herein or otherwise useful in synthetic organic chemistry and/or electrochemical detection.

Materials:

All chemicals were analytical grade and used without further purification. 2,4,6-trinitrotoluene, 2,4-dinitrotoluene, 2,6-dinitrotoluene, and nitrobenzene, $ZnNO_3 \cdot 6H_2O$, 2-methylimidazole, toluene, 4-nitrophenol, $Pb^{2+}$, potassium chloride, Nafion®-brand resin (registered trademark of E.I. du Pont de Nemours & Co.), and urea were obtained from Sigma-Aldrich (St. Louis, Mo.) and Fisher Scientific (Pittsburgh, Pa.). Deionized water generated by a Millipore Milli-Q system (MilliporeSigma, Burlington, Mass.; resistivity 18.2 MΩ-cm) was used in the electrochemical studies.

Material Characterizations:

X-ray diffraction (XRD) analysis was investigated with a PANalytical X'PERT PRO X-ray diffractometer using CuKα radiations λ=0.1542 nm, 40 kV, 20 mA (PANalytical B.V., Almelo, Netherlands). Transmission electron microscopy (TEM) was performed using a JEOL JEM-2100F electron microscope (JEOL, Akishima, Japan). $N_2$ adsorption studies were performed on an Autosorb®-brand instrument at 77 K (Quantachrome Instruments, Boynton Beach, Florid). All the samples were degassed at 423 K under vacuum before analysis. Atomic force microscopy (AFM) images were taken in tapping mode using an Asylum Research, Cypher S-brand instrument. (Asylum Research, a wholly owned subsidiary of Oxford Instruments, Santa Barbara, Calif.). Zeta potential measurements were carried out using a NanoBrook® 90Plus-brand particle analyzer (Brookhaven Instruments Corp., Holtsville, N.Y.).

Preparation of Solutions:

All solutions were made with analytical grade chemicals in ultra-purified water from a Milli-Q system (Millipore). In all the experiments, the supporting electrolyte was 0.5 M potassium chloride solution. Stock solutions of nitroaromatic explosives were prepared carefully in a ventilating hood and were successively diluted to obtain the desired concentration range.

Synthesis of ZIF-8:

A novel one-step method was developed to prepare ZIF-8 crystals. In a typical synthesis, 20 mg of zinc nitrate hexahydrate dispersed in 1 mL Millipore water (0.067 M $Zn(NO_3)_2$) was added to a solution of 2-methylimidazole (2.3 g, ~28 mM) in 9 g Millipore water under stirring. The mixture turns turbid immediately; after 2 min of stirring, the nanocrystals were separated from the milky dispersion by centrifugation at 8000 rpm for 30 min and dried overnight at 333 K.

TNT Vapor Generation:

A known amount of TNT was placed in 5 mL borosilicate glass under a heating mantle set at 80° C. The top of the borosilicate glass was covered by an aluminum foil and then capped. The disposable screen-printed electrode (described below) was fitted to the top of the glass vessel.

Electrochemical Measurements:

Electrochemical experiments were performed using CHI-660D electrochemical workstation (CHI Instruments Inc., Austin, Tex.) using a disposable screen-printed electrode (SPE). The electrode pattern comprised a 3-mm diameter carbon working electrode, a carbon counter electrode, and a silver/silver chloride reference electrode.

Electrode Fabrication:

Catalyst ink was prepared by mixing 5.0 mg of the prepared ZIF-8 catalyst with a mixture of 100 µl Nafion®-brand resin (0.5 wt %) and 0.9 mL of water, thereafter dispersed by sonication for 1 hour to obtain a well-dispersed suspension. 2 µL of the catalyst ink was drop-cast onto the SPE surface. The electrode was then dried in air leaving the material mounted onto the SPE surface.

Figure 1B:
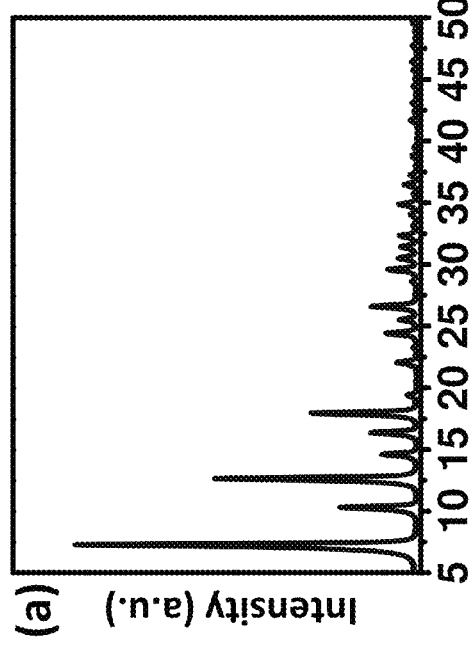

Characterization of the ZIF and Method to Detect Nitro-Aromatic Explosives:

Powder X-ray diffraction (XRD) has been exploited to confirm the crystal structure and to investigate the phase of the prepared material. See FIG. 1A, which is the full X-ray diffractogram for a specimen of the ZIF-8 made as described herein. The XRD peaks of ZIF-8 as shown in FIG. 1A match to a sodalite topology. [21-23] A very sharp peak at 7.2° on the XRD diffractogram of FIG. 1A indicates that ZIF-8 is highly crystalline. Furthermore, the XRD patterns of the ZIF-8 exhibited a better crystallinity as compared to that of silica-based materials such as SBA-15. The nitrogen isotherm of ZIF-8, shown in FIG. 1B displayed a type-1 isotherm typical for microporous materials. The capillary step in the $p/p_0$ (<0.1) suggests a microporous structure according to IUPAC classification.[23,24] The BET-specific surface area of 1398.7 $m^2/g$ and cumulative pore volume of 0.62 $cm^3/g$ were obtained for ZIF-8 when made as described herein. The pore-size distribution was determined using the Barrette Joynere Halenda method, showing a mean pore size distributed between 0.4 nm and 1.8 nm which implies that the material is microporous (<2 nm), see FIG. 1B.[23,24] The nitrogen adsorption/desorption parameters of the ZIF-8 are summarized in Table 1.

TABLE 1

Surface properties of synthesized material.

| Sample | Total surface area ($m^2 g^{-1}$) | External surface area ($m^2 g^{-1}$) | Micropore area ($m^2 g^{-1}$) | Micropore volume ($cm^3 g^{-1}$) |
|---|---|---|---|---|
| ZIF-8 | 1398.75 | 94.57 | 1304.17 | 0.6236 |

Figure 1C:
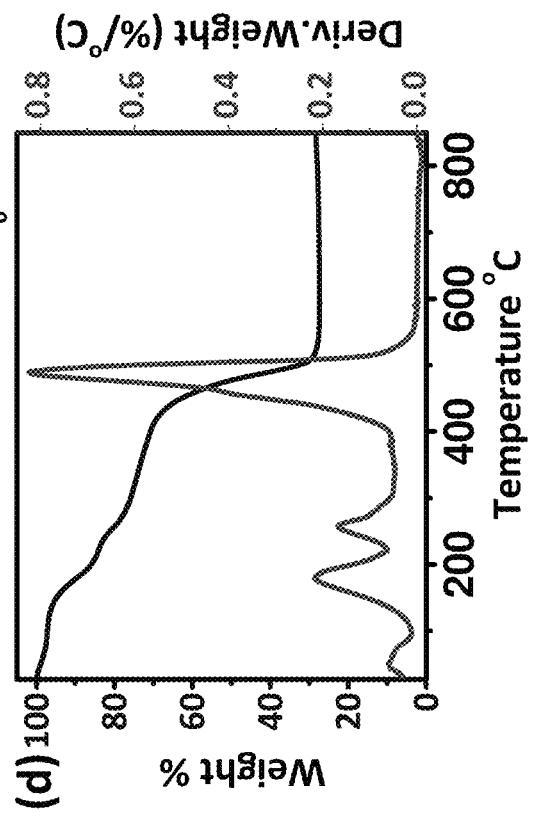
Figure 1D:
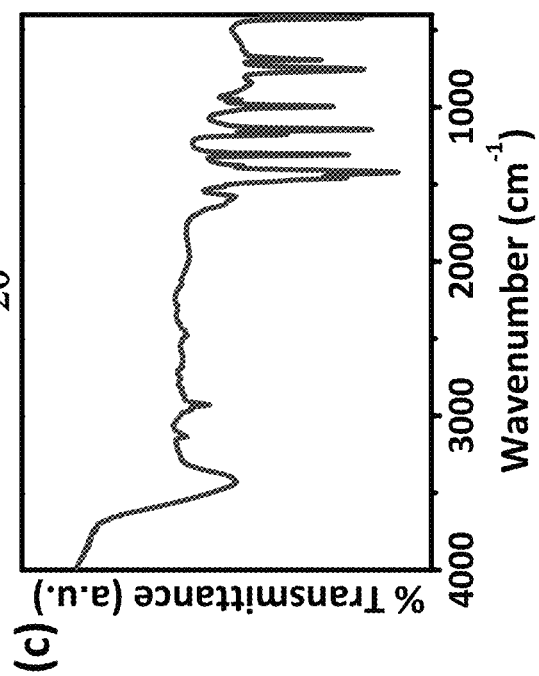

The chemical state of the synthesized material was further investigated by FT-IR. FT-IR spectra of ZIF-8 showed a characteristic peak in the frequency region from 900-1350 $cm^{-1}$ which can be attributed to in-plane bending of the imidazole ring. See FIG. 1C. The bands between 800 to 400 $cm^{-1}$ are associated with the out-of-plane bending of the ring. The band at 1582 $cm^{-1}$ is due to the C≡N stretching mode. The signal at 417 $cm^{-1}$ is ascribed to the stretching vibrations of Zn—N. The thermogravimetric analysis (TGA) profile of ZIF-8 showed weight loss below 200° C. which is attributed to the removal of adsorbed water molecules from the cavities. See FIG. 1D. The second loss observed above 200° C. corresponds to the carbonization of unreacted 2-methylimidazole. A sharp weight loss step at about 490° C. corresponds to the decomposition of the ZIF-8 nanocrystal.

The morphologies of the as-prepared ZIF-8 have been examined by transmission electron microscopy (TEM). See FIGS. 2A and 2B, which are panoramic images of a representative ZIF-8 sample. FIGS. 2A and 2B reveal a highly ordered hexagonal symmetry. The ZIF-8 crystallites are in the size range of ~380 nm on average. As shown in FIG. 2C, a two-dimensional atomic force microscopy (AFM) topographic image clearly reveals the hexagonal edges of a single crystal. The AFM image in FIG. 2C is confirms the accuracy of the SEM and TEM images. The topographic profile indicates a high aspect ratio of the crystals, with a height of about ~60 nm, as shown in FIG. 2D.

Figure 3B:
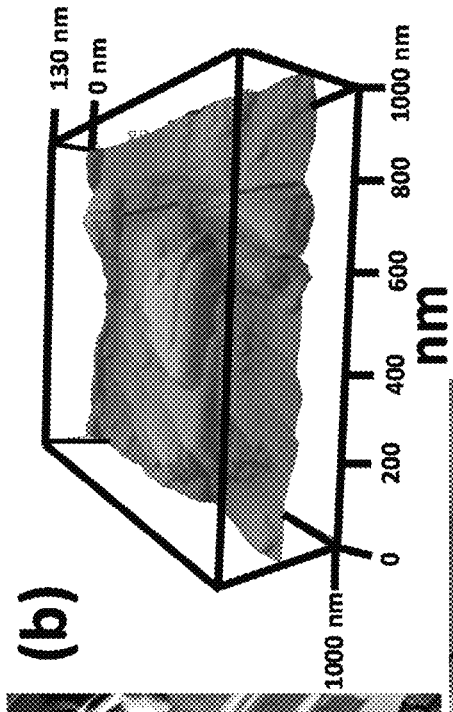
FIG. 3A is a real-time AFM 2D image and FIG. 3B is a representative AFM 3-D image of growing ZIF-8 crystal taken 1 minute after first observing surface nuclei.
Figure 3A:
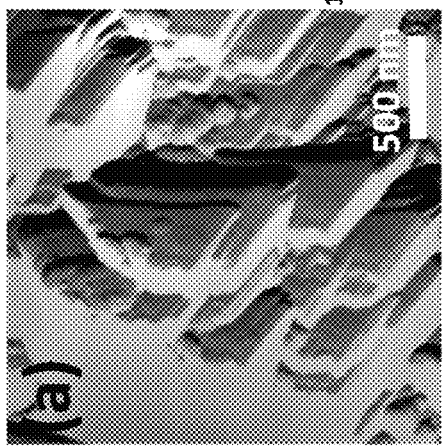
Figure 3C:
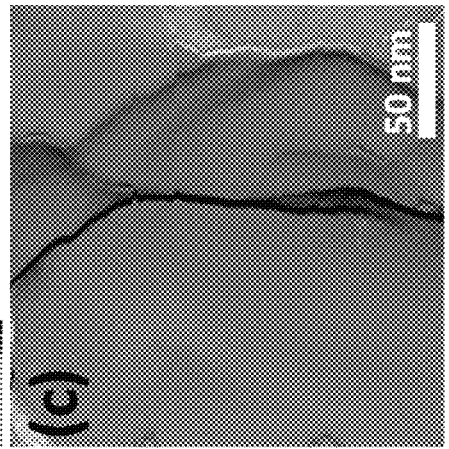
FIG. 3C is a real-time AFM 2D image taken 2 minutes after first observing surface nuclei.

The AFM images of ZIF-8 at different reaction times are shown in FIGS. 3A, 3B, and 3C. The crystal surface at 1 minute, shown 2-dimensionally in FIG. 3A and 3-dimensionally shows the beginning of the formation of a highly ordered hexagonal symmetry. The atomic force microscopy image taken at 2 minutes, shown in FIG. 3C, confirms the ordered hexagonal symmetry.

XPS studies have been further performed to characterize the chemical composition of the ZIF-8 manufactured as described herein. See FIGS. 4A-4E. The wide scan spectra from ZIF-8, shown in FIG. 4A, shows multiple regions of Zn 2p, O 1s, N and 1s, respectively. Individual spectra for each element (N 1s, Zn 2p, O 1s, and C 1s) were collected over the appropriate energy range. See FIGS. 4B-4E. The high-resolution N1s spectra of ZIF-8, FIG. 4B, exhibited peaks of 399.5 and 407.1 eV, which corresponded to pyridinic nitrogen C—N=, and C—NH— graphitic-nitrogen, respectively.[25] The high-resolution Zn 2p XPS scan shows Zn 2p3/2 and Zn 2p1/2 subpeaks of the Zn 2p doublet, which were located at 1022.24 and 1045.34 eV, confirmed the position of the metallic Zn 2p peaks.[25] See FIG. 4C. The O is spectra is shown in FIG. 4D. The peaks with binding energy of 531.4 is assigned to the 0 in the forms of Zn—OH (FIG. 4D). The peaks in the C1s area, see FIG. 4E, are very likely from imidazole-derived carbon. Overall, the XPS analysis, together with the FTIR and XRD data, confirmed the formation of ZIF-8.

The growth of ZIF-8 nanocrystals was monitored by tracking the change in solution pH with reaction time. The initial pH of aqueous $H_2O$ was 7.4, which increased to 11.4 when 2-methylimidazole (Hmim) precursor was added; however, upon further addition of $Zn^{2+}$ solution, the pH decreased to 10.8 in 60 s and to 10.42 in 120 s. The pH remained constant thereafter confirming that the formation of ZIF-8 crystal is complete. The initial drop in pH of the synthesis solution can be assigned to the acidity introduced by the zinc solution and the ligand deprotonation during the reaction. When $Zn^{2+}$ is added, coordination of $Zn^{2+}$ to the ligand occurs at the nitrogen atoms at positions 1 and 3 in imidazole. Here Hmim act as a linker unit in its deprotonated form. The drop in the pH shows nucleation as well as a fast crystallization rate which is reflected by the change in turbidity of the solution after 60 s. The product formed is rhombic dodecahedron in morphology and its crystalline shape is determined by the discrepancies in the growth rates. The growth rate is associated with the degree of nucleation as well as the fast crystallization rate.

Figures 10A, 10B:
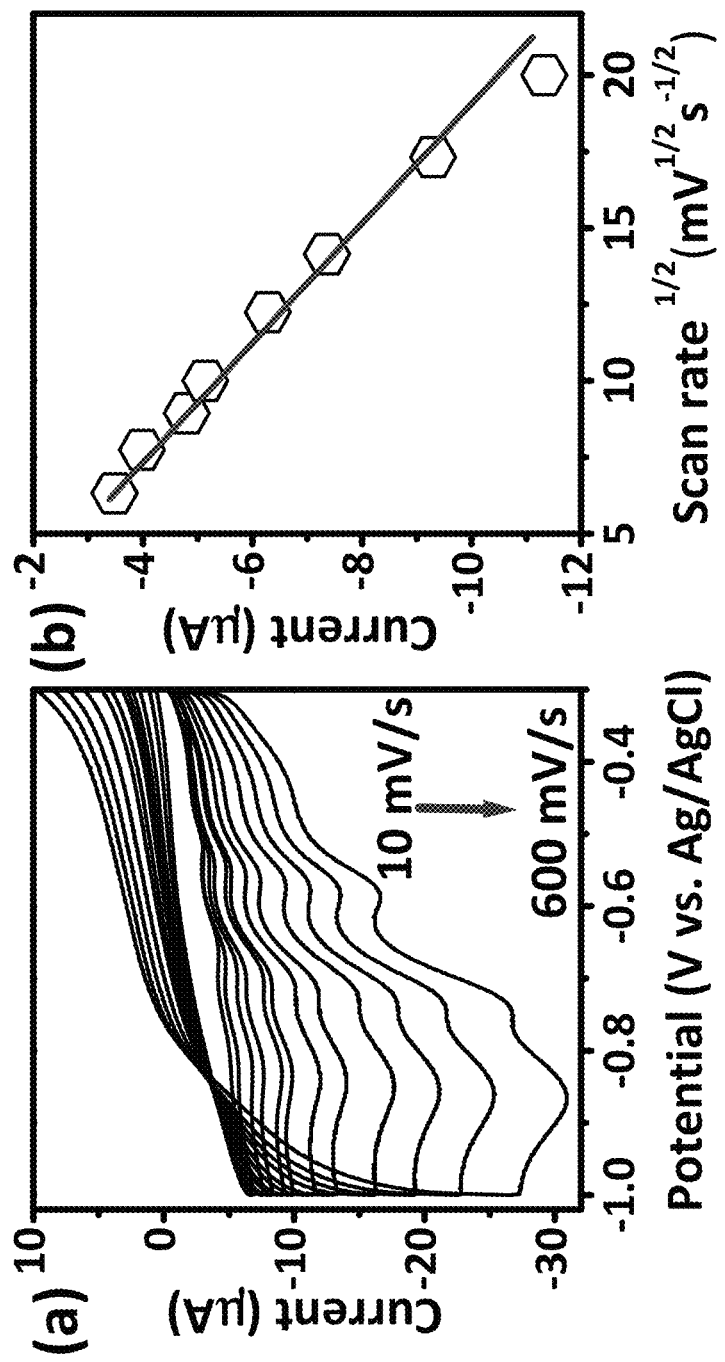
FIG. 10A shows cyclic voltammetry (CV) plots of TNT (50 μM) at various scan rates (10-600 $mVs^{-1}$) using the ZIF-8-modified electrode disclosed herein.
FIG. 10B is plot of peak currents vs. the square root of the scans.
Figure 11:
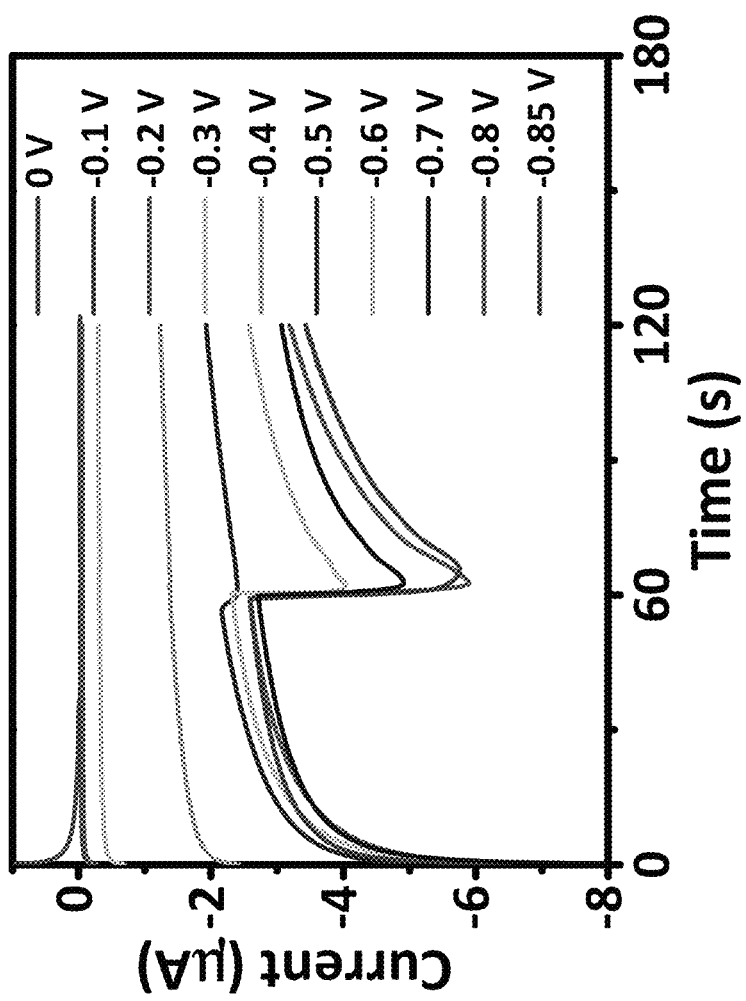
FIG. 11 presents current-time curves for the ZIF-8-modified electrode upon ten (10) successive additions of TNT (200 nM) with different applied potentials ranging from 0 to −0.85 V.

The utility of the ZIF-8-modified electrode for nitro-aromatic explosive detection was then explored. The electrochemical behavior of TNT was first investigated by cyclic voltammetry. As seen in FIG. 10A, the reduction peak current of TNT increases with an increase in scan rate. The reduction peak current was in linear relation with the square root of scan rate from 40 to 400 mV $s^{-1}$, as shown in FIG. 10B. The non-zero intercept (FIG. 10B) suggested that TNT is initially adsorbed at the surface-active sites. The effect of applied potential on the reduction peak current (i-t curve) for 200 nM aqueous TNT solution was investigated. The amperometric response of ZIF-8 modified electrode (0 mV to −850 mV range) was recorded upon 10 successive additions of TNT solution. The results are shown in FIG. 11. The results showed applied potentials ranging from −0.40 to −0.85 V accelerated the reduction current providing the best values of TNT reduction. The maximum response current with a good signal/noise ratio was achieved at 0.8 V. Thus, a constant potential of −0.8 V was chosen for further amperometric investigations.

Figure 5E:
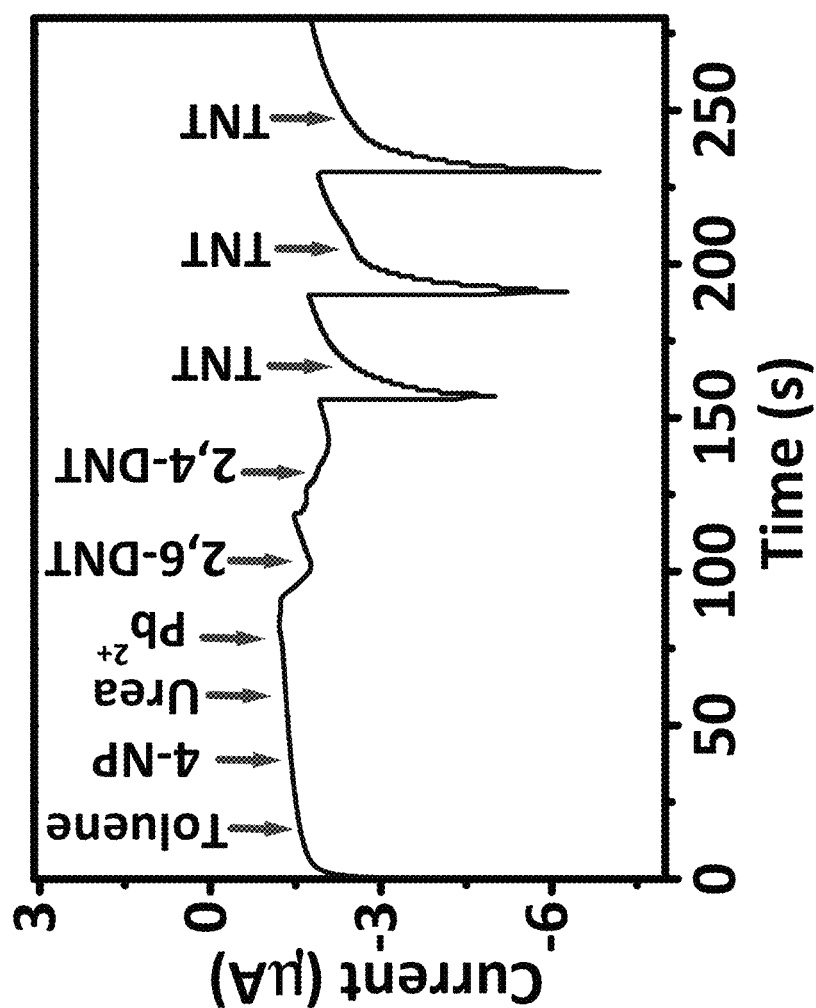
FIG. 5E depicts a continuous amperometric response at ZIF-8-modified electrode to different interfering species each spiked at 500 μM and TNT at 50 nM concentration.

The electrochemical behavior of TNT with respect to the ZIF-8-modified electrode described herein was first investigated by pulse amperometry. FIG. 5A illustrates the three-step potential pulse amperometric response obtained for ten injections of a standard solution of TNT (ranging from 0 nM TNT to 175 nM TNT) at a fixed potential (−0.8 V). As clearly shown in FIG. 5A, the ZIF-8 modified electrode exhibited reduction peak current densities that are proportional to the TNT concentration. The precision of the sensor was then investigated by pulse amperometric response at a fixed potential (−0.8 V) in response to adding TNT (50 nM) (See FIG. 5B). The test revealed that the 50 cycles showed no current drop. The inset of FIG. 5B shows an enlarged view. Surface zeta potential measurements were then used as a means to investigate the electrostatic interactions between ZIF-8 nanoparticles with TNT.[26] The zeta potential value of water was measured to be 0 mV at pH=7. See FIG. 5C. In the presence of TNT, a zeta potential value of −28.8 mV was seen, implying a negative surface charge. ZIF-8 dispersed in water has a zeta potential value of −9.9 mV. Adding TNT to ZIF-8 induces a lower value of zeta potential (−16.8 mV), thus clearly indicate the electrostatic interaction (adsorption) between TNT and ZIF-8. See FIG. 5D5E.

To understand the interface reactions further, electrochemical impedance spectroscopy (EIS) measurements were performed. Bode module plots at open circuit in the presence and absence of TNT can be considered to have two regions, one at high frequency corresponding to the depletion layer, and another at low frequency relating to the Helmholtz layer (See FIG. 5D). The increase in phase angle after adding 80 nM of TNT (−42°) in the low-frequency region consisted predominantly of capacitive reactance but was far less than −90°, which is associated with the interaction between TNT and the ZIF-8-modified electrode.

Figure 6:
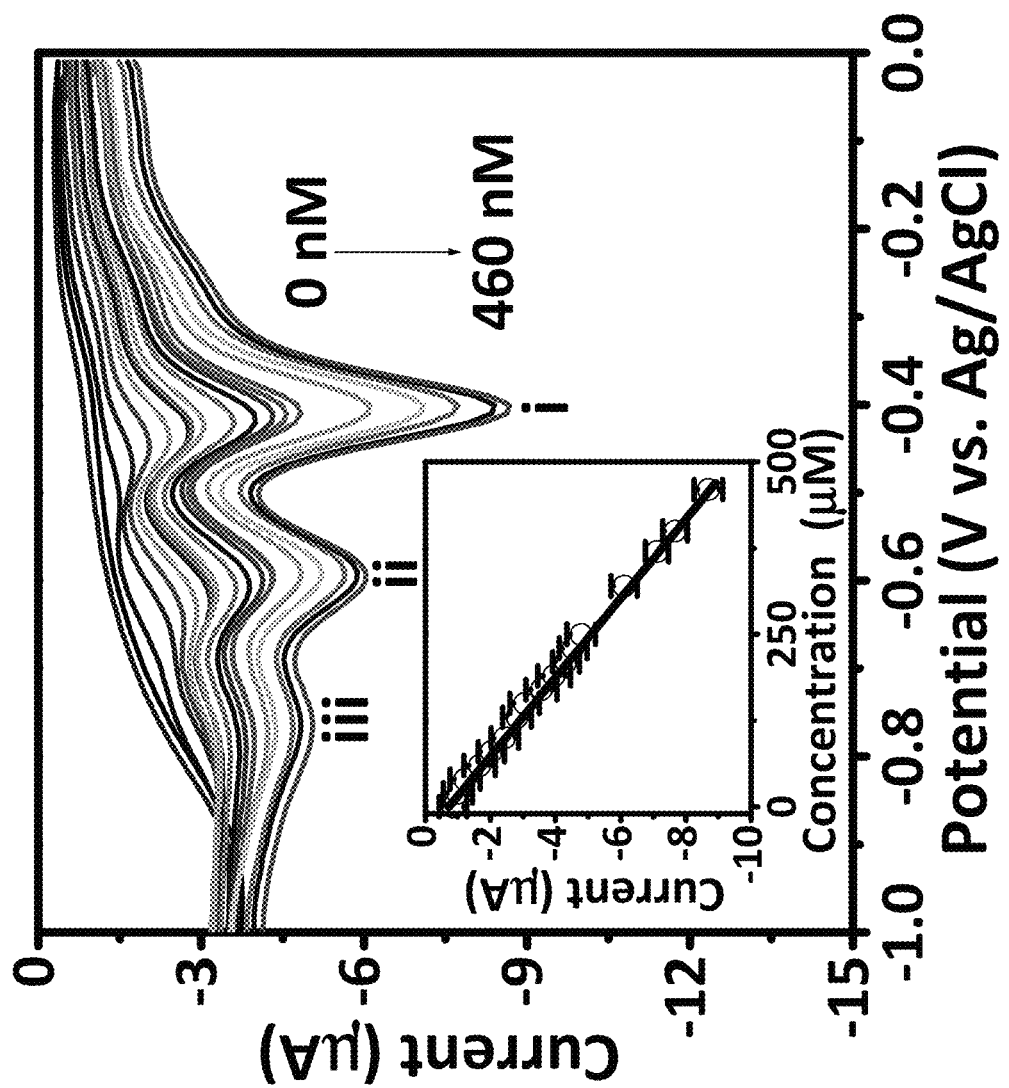
FIG. 6 shows the results of differential pulse voltammetry (DPV) with varying concentrations of TNT at the ZIF-8-modified electrode. The inset displays the calibration curve. DPV parameters: peak width=0.2 s; pulse period=0.5 s; increment=10 mV.

Contacting the ZIF-8-modified electrode with various concentrations of TNT and then performing differential pulse voltammetry (DPV) shows that the resulting curves are concentration-dependent. See FIG. 6. The clearly demonstrates that the electrode as described herein can be used to detect TNT. Here, the concentration of the TNT solution was serially diluted from 0 nM to 460 nM. The inset of FIG. 6 displays the calibration curve. The DPV test parameters were as follows: peak width=0.2 s; Pulse period=0.5 s; increment=10 mV. More specifically, a linear range over a TNT concentration from 1 nM to 460 nM with a detection limit of 346 pM was obtained (level of detection=3σ/S, where (σ) the standard deviation of the three-parallel analysis of the blank, and (S) the slope of the calibration line).[27] Again, see FIG. 6. The linear regression equation was I (μA)=−0.0174−0.6249 $C_{TNT}$ (nM), ($R^2$=0.9981). The analytical parameters of the ZIF-8-modified electrode was compared with different methods previously reported for DNB, DNT, and TNT detection in the literature.[28-50] The results are presented in Table 2. The sensor described herein has a demonstrated level of detection and a rational linear range suitable for the detection of TNT as compared to known assay methods (as shown in Table 2).

TABLE 2

Analytical performance comparison of ZIF-8 modified electrode with sensors reported for detection of DNT, DNB, and TNT.

| Procedure | Technique | Analyte | Linear Range (nM) | Detection Limit (nM) | References |
|---|---|---|---|---|---|
| $NH_3$-plasma-treated MWCNT/GCE | SWV | DNT | $8.9 \times 10^2$-$5.34 \times 10^3$ | 0.6394 | 28 |
| Reduced graphene/GCE | LSV | DNT | $5.49 \times 10^4$-$11.0 \times 10^4$ | 42 | 29 |
| Poly[meso-tetrakis(2-thienyl)porphyrin]/GCE | DPV | DNT | — | 8 ppb | 30 |
| $NH_3$-plasma-treated MWCNTs | SWASV | DNT | $1.0 \times 10^2$-$1.0 \times 10^3$ | 0.12 | 31 |
| Polyaniline Nanofibers/GCE | DPV | DNB | 22-$3.08 \times 10^3$ | 7.33 | 32 |
| Porphyrin/CNTs/GCE | DPV | DNB | 9-$5.0 \times 10^4$ | 2 | 33 |
| Two-dimensional MIM/Au nanoparticles/GCE | DPV | TNT | 40-$3.2 \times 10^3$ | 13 | 34 |
| Acrylic polymer (MIP) electrode | DPV | TNT | $5.0 \times 10^2$-$2.0 \times 10^4$ | 500 | 35 |
| MIP/MWCNTs/GCE | SWV | DNB | 45-$8.5 \times 10^3$ | 25.15 | 36 |
| Ordered mesoporous carbon | ASV | DNT | — | 5.5 | 37 |
| Nitrogen-doped graphene/GCE | LSV | TNT | 528-$8.8 \times 10^3$ | 130 | 38 |
| Nano-MIP/$Fe_3O_4$NPs based MCPE | SWV | TNT | 1.00-130.00 | — | 39 |
| Gr-PANI-MIP film | DPV | TNT | 730.00-$3.15 \times 10^3$ | — | 40 |
| Anion exchanger resin | UV-vis | TNT | $1.76 \times 10^3$-$5.10 \times 10^5$ | $127 \times 10^3$ | 41 |
| DLLME | GC-MS | TNT | 12.76-127.68 | 2.17 | 42 |
| Metalloporphyrin-functionalised diamond NPs | SAW | TNT | 140.44-$3.06 \times 10^3$ | 12.76 | 43 |
| AuNPs based | SERS | TNT | 0.10-100.00 | 0.10 | 44 |
| CL-ELISA | Luminor | TNT | — | 5.11 | 45 |
| CL-labeled immunosensor | CL | TNT | (2.55-63.84) $\times 10^3$ | $2.55 \times 10^3$ | 46 |
| Enzyme Immunosensor | ECL | TNT | — | 1.40 | 47 |
| Graphene | CV | TNT | $12.76 \times 10^3$-$24.25 \times 10^5$ | $12.76 \times 10^3$ | 48 |

TABLE 2-continued

Analytical performance comparison of ZIF-8 modified electrode with sensors reported for detection of DNT, DNB, and TNT.

| Procedure | Technique | Analyte | Linear Range (nM) | Detection Limit (nM) | References |
|---|---|---|---|---|---|
| FRET | Fluorescence | TNT | 3.19-191.52 | 0.29 | 49 |
| AuNPs nanoplasmonic probe | PRET | TNT | 2.55-2.55 × $10^3$ | 2.55 | 50 |
| ZIF-8 | DPV | TNT | 1-460 | 346 pM | This work |

Abbreviations:
Linear sweep voltammetry (LSV),
Squarewave voltammetry (SWV),
Differential pulse voltammetry (DPV),
Adsorptive stripping voltammetry (ASV),
Square-Wave Anodic Stripping Voltammetry (SWASV),
glassy carbon electrode (GCE),
Dinitrobenzene (DNB),
Multi-walled Carbon Nanotubes (MWCNT),
Molecular Imprinting (MIM),
Molecular imprinting polymer (MIP),
Dispersive liquid-liquid microextraction (DLLME),
Chemiluminescence enzyme-linked immunosorbent assay (CL-ELISA),
Forster resonance energy transfer (FRET).

Figure 7:
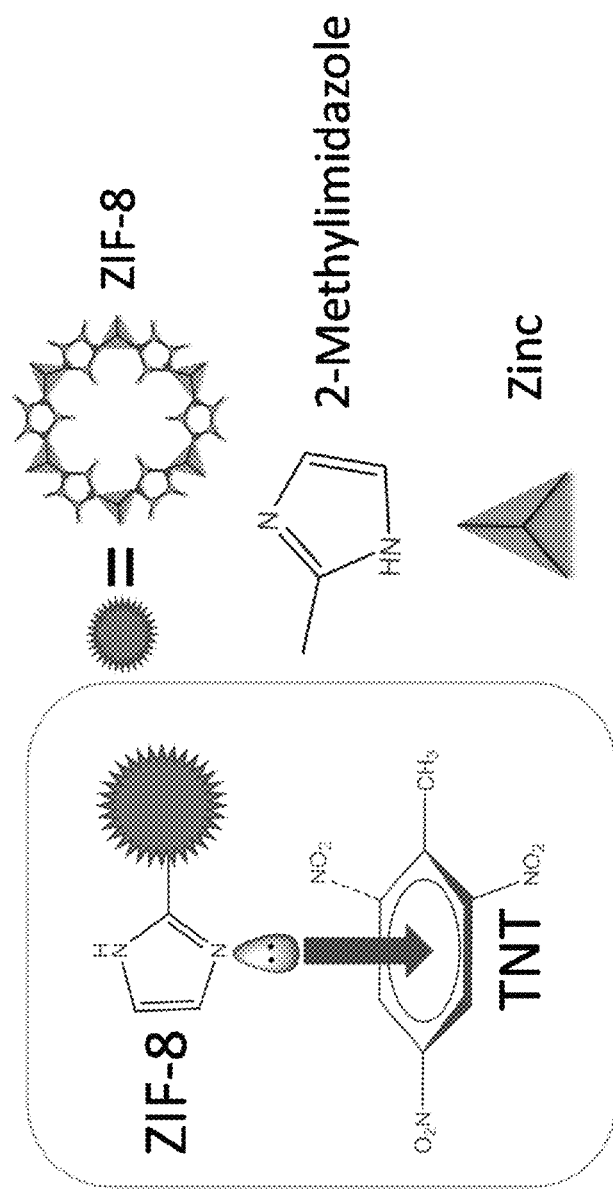
FIG. 7 is a schematic diagram of the charge-transfer complex interactions between ZIF-8 and the TNT molecule.

While not being bound to any underlying mechanism or phenomenon, it is believed that the TNT molecule interacts with the ZIF-8 as shown schematically in FIG. 7. As shown in FIG. 7, it is believed that the lone pair electrons on the nitrogen atoms of the imidazole rings of the ZIF-8 coordinate with the delocalized aromatic electrons of the toluene ring of TNT, thus binding TNT molecules with the ZIF-8. This is further bolstered by FT-IR studies, which confirmed the presence of an aromatic ring in ZIF-8. TNT is an electron-deficient molecule because of three electron-withdrawing nitro groups and the electron-rich ZIF-8 (lone pair electrons on the nitrogen atoms) which favors the formation of donor-acceptor electron-transfer mechanism.

The specificity of different substances as potential interfering compound for the determination of TNT was studied under the optimum conditions. It was found that the ZIF-8-modified electrode displayed excellent anti-interference properties towards possible co-existing organic molecules and inorganic cations in water and soil. The results also showed that 500 µM concentrations of toluene, urea, 4-nitrophenol, and $Pb^{2+}$ did not interfere with the detection of TNT (see FIG. 5E).

The electrochemical responses of the ZIF-8-modified electrode to a series of nitroaromatic compounds, including nitrobenzene (NB), 2,6-dinitrotoluene (2,6-DNT), and 2,4-dinitrotoluene (2,4-DNT) were investigated. The results are shown in FIGS. 8A (NB), 8B (2,6-DNT), 8C (TNT), and 8D (2,4-DNT). It was observed that the position of cathodic peaks is strongly dependent on the number of nitro groups contained in nitroaromatic compounds. Nitrobenzene (FIG. 8A) exhibits only one reduction peaked at −0.83 V. In contrast, 2,4-DNT (FIG. 8D) and 2,6-DNT (FIG. 8B) exhibit two reduction peaks, showing that the sensor can detect the other nitroaromatic explosive with high sensitivity. FIG. 8C shows the corresponding curve for TNT for sake of comparison.

Figure 12:
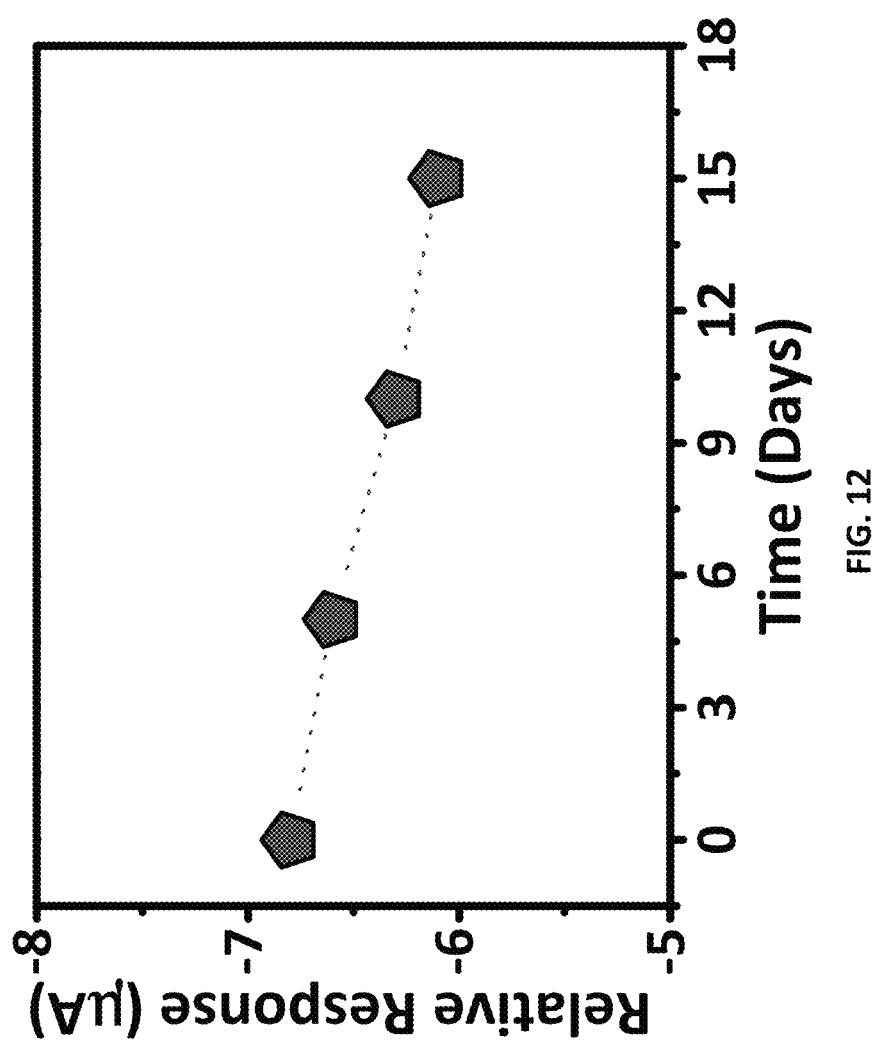
FIG. 12 is a graph showing the stability (i.e., relative response over time) for the ZIF-8-modified electrode to 100 nM TNT over the course of 15 days.

The storage stability of the ZIF-8 modified electrode was studied by measuring the sensor response to TNT over time. The results are shown in FIG. 12. There was no obvious decrease in the normalized signal to 100 nM TNT for a period of 15 days. Over that time period, the sensor retained 89.7% of its initial signal, indicating the acceptable stability. In addition, it was found that the standard deviation of current responses obtained at two different electrodes prepared by the same method for 100 nM did not exceed 6.2%.

The structural change induced by the TNT reduction reaction at a ZIF-8-modified screen-printed electrode surface was investigated by scanning electron microscopy (SEM). The bare SPE surface is not covered by carbon particles; however, after modification ZIF-8 nanoparticles are seen distributed throughout the SPE surface. (Data not shown). The ZIF-8 nanoparticles octahedral in shape.

Figure 9B:
FIG. 9B shows the electrode housed in a measurement chamber containing TNT vapors.
Figure 9D:
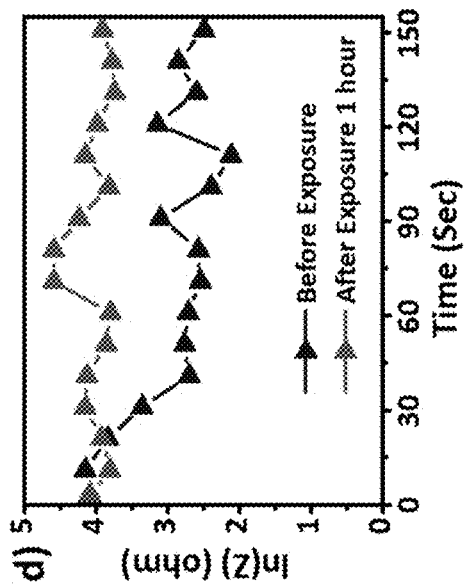
FIG. 9D shows impedance (Z) versus time before exposure to TNT vapors and after exposure to TNT vapors for one hour.
Figure 9A:
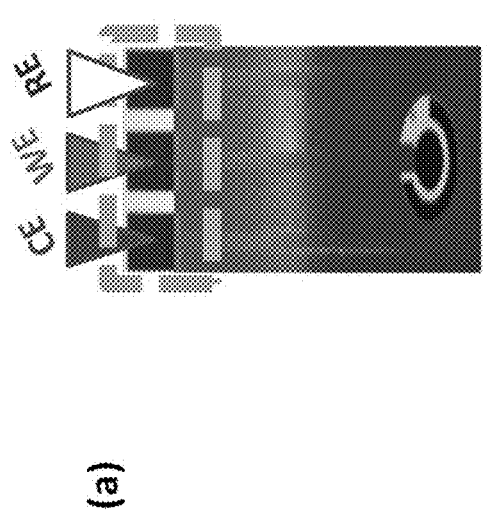
FIG. 9A shows the gas-phase detection of TNT using a ZIF-8-functionalized screen-printed electrode.
Figure 9C:
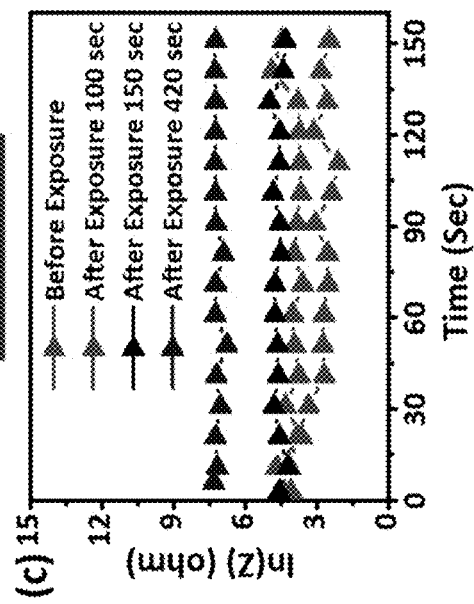
FIG. 9C shows impedance (Z) versus time before exposure to TNT vapors and after exposure to TNT vapors for up to 420 seconds.

The method to detect nitro-aromatic explosives using the ZIF-8-modified electrode thus has high sensitivity and good selectivity for the detection of TNT and other nitro-aromatic vapors. TNT has an extremely low volatility (vapor pressure $4.8 \times 10^{-6}$ Torr) at 20° C. Therefore, TNT residues are expected to persist and evaporate over time.[51] Thus, the resistance response sensitivities for the ZIF-8 sensor upon exposure to TNT vapors as a function of exposure time was evaluated. The ZIF-8-modified electrode is shown in FIG. 9A. A sealed vial (5 mL) was filled with a known amount of solid explosive and the electrode inserted, as shown in FIG. 9B. Exposure of TNT vapors was achieved by placing the ZIF-8-modified electrode into the sealed vial at a chosen temperature (about 80° C. in this experiment). After exposing the electrode for a given period of time, the resistance values of the electrode were measured. The results for exposure times up to 420 seconds are shown in FIG. 9C. The results for an exposure time of 1 hour are shown in FIG. 9D. The response of the sensor to the presence of TNT vapors was instantaneous with an increase in resistance values upon time. The current intensity of the ZIF-8 sensor was also recorded after exposure to the saturated vapours of TNT at room temperature for 1 h (FIG. 9D). The resistance gradually increased. These results show that the electrode described herein is a sensitive electrochemical sensor for detecting TNT vapors.

In closing, disclosed herein is an easy approach to synthesize high-quality ZIF-8. The method enables rapid, large-scale, low-cost preparation of ZIF-8. The electrode described herein is useful for detecting nitro-aromatic explosives. The linear range of detection is from about 1 nM to about 460 nM, and the limit of detection is 346 pM. Zeta potential studies and electrochemical studies further prove that TNT molecule adsorbs onto the ZIF-8 hexagonal nanosheet. The practical utility of the sensor was also demonstrated in the gas phase.

REFERENCES

The following documents are incorporated herein by reference.
(1) Furukawa, H.; Cordova, K. E.; O'Keeffe, M.; Yaghi, O. M. The Chemistry and Applications of Metal-Organic Frameworks. Science 2010, 9 (6149), 1230444.
(2) Rosi, N. L.; Eckert, J.; Eddaoudi, M.; Vodak, D. T.; Kim, J.; O'Keeffe, M.; Yaghi, O. M. Hydrogen Storage in Microporous Metal-Organic Frameworks. Science 2003, 300 (5622), 1127-1129.
(3) Li, J.-R.; Kuppler, R. J.; Zhou, H.-C. Selective Gas Adsorption and Separation in Metal-organic Frameworks. Chem. Soc. Rev. 2009, 38 (5), 1477.
(4) Lee, J.; Farha, O. K.; Roberts, J.; Scheidt, K. A.; Nguyen, S. T.; Hupp, J. T. Metal-Organic Framework Materials as Catalysts. Chem. Soc. Rev. 2009, 38 (5), 1450-1459.
(5) Bétard, A.; Fischer, R. A. Metal-Organic Framework Thin Films: From Fundamentals to Applications. Chemical Reviews. 2012, pp 1055-1083.
(6) Chaikittisilp, W.; Hu, M.; Wang, H.; Huang, H.-S.; Fujita, T.; Wu, K. C.-W.; Chen, L.-C.; Yamauchi, Y.; Ariga, K. Nanoporous Carbons through Direct Carbonization of a Zeolitic Imidazolate Framework for Supercapacitor Electrodes. Chem. Commun. 2012, 48 (58), 7259.
(7) Yaghi, O. M.; Davis, C. E.; Li, G.; Li, H. Selective Guest Binding by Tailored Channels in a 3-D Porous zinc(II)-Benzenetricarboxylate Network. J. Am. Chem. Soc. 1997, 119 (12), 2861-2868.
(8) Gross, A. F.; Sherman, E.; Vajo, J. J. Aqueous Room Temperature Synthesis of Cobalt and Zinc Sodalite Zeolitic Imidizolate Frameworks. Dalt. Trans. 2012, 41 (18), 5458.
(9) Zhang, H. X.; Cao, A. M.; Hu, J. S.; Wan, L. J.; Lee, S. T. Electrochemical Sensor for Detecting Ultratrace Nitroaromatic Compounds Using Mesoporous $SiO_2$-Modified Electrode. Anal. Chem. 2006, 78 (6), 1967-1971.
(10) Zang, J.; Guo, C. X.; Hu, F.; Yu, L.; Li, C. M. Electrochemical Detection of Ultratrace Nitroaromatic Explosives Using Ordered Mesoporous Carbon. Anal. Chim. Acta 2011, 683 (2), 187-191.
(11) Yan, F.; He, Y.; Ding, L.; Su, B. Highly Ordered Binary Assembly of Silica Mesochannels and Surfactant Micelles for Extraction and Electrochemical Analysis of Trace Nitroaromatic Explosives and Pesticides. Anal. Chem. 2015, 87 (8), 4436-4441.
(12) Stringer, R. C.; Gangopadhyay, S.; Grant, S. A. Detection of Nitroaromatic Explosives Using a Fluorescent-Labeled Imprinted Polymer. Anal. Chem. 2010, 82 (10), 4015-4019.
(13) Salinas, Y.; Agostini, A.; Pérez-Esteve, É.; Martínez-Máñez, R.; Sancenón, F.; Dolores Marcos, M.; Soto, J.; Costero, A. M.; Gil, S.; Parra, M.; Amorós, P. Fluorogenic Detection of Tetryl and TNT Explosives Using Nanoscopic-Capped Mesoporous Hybrid Materials. J. Mater. Chem. A 2013, 1 (11), 3561.
(14) Anu Prathap, M. U.; Wei, C.; Sun, S.; Xu, Z. J. A New Insight into Electrochemical Detection of Eugenol by Hierarchical Sheaf-like Mesoporous $NiCo_2O_4$. Nano Res. 2015, 8 (8), 2636-2645.
(15) Prathap, M. U. A.; Sun, S.; Wei, C.; Xu, Z. J. A Novel Non-Enzymatic Lindane Sensor Based on CuO—$MnO_2$ Hierarchical Nano-Microstructures for Enhanced Sensitivity. Chem. Commun. 2015, 51, 4376-4379.
(16) Anu Prathap, M. U.; Srivastava, R. Synthesis of $NiCo_2O_4$ and Its Application in the Electrocatalytic Oxidation of Methanol. Nano Energy 2013, 2 (5), 1046-1053.
(17) Anu Prathap, M. U.; Chaurasia, A. K.; Sawant, S. N.; Apte, S. K. Polyaniline-Based Highly Sensitive Microbial Biosensor for Selective Detection of Lindane. Anal. Chem. 2012, 84 (15), 6672-6678.
(18) Seenivasan, R.; Chang, W.-J.; Gunasekaran, S. Highly Sensitive Detection and Removal of Lead Ions in Water Using Cysteine-Functionalized Graphene Oxide/Polypyrrole Nanocomposite Film Electrode. ACS Appl. Mater. Interfaces 2015, 7 (29), 15935-15943.
(19) Seenivasan, R.; Maddodi, N.; Setaluri, V.; Gunasekaran, S. An Electrochemical Immunosensing Method for Detecting Melanoma Cells. Biosens. Bioelectron. 2015, 68, 508-515.
(20) Seenivasan, R.; Singh, C. K.; Warrick, J. W.; Ahmad, N.; Gunasekaran, S. Microfluidic-Integrated Patterned ITO Immunosensor for Rapid Detection of Prostate-Specific Membrane Antigen Biomarker in Prostate Cancer. Biosens. Bioelectron. 2017, 95, 160-167.
(21) He, M.; Yao, J.; Liu, Q.; Wang, K.; Chen, F.; Wang, H. Facile Synthesis of Zeolitic Imidazolate Framework-8 from a Concentrated Aqueous Solution. Microporous Mesoporous Mater. 2014, 184, 55-60.
(22) Tu, M.; Wiktor, C.; Rösier, C.; Fischer, R. A. Rapid Room Temperature Syntheses of Zeolitic-Imidazolate Framework (ZIF) Nanocrystals. Chem. Commun. 2014, 50 (87), 13258-13260.
(23) Ren, H.; Zhang, L.; An, J.; Wang, T.; Li, L.; Si, X.; He, L.; Wu, X.; Wang, C.; Su, Z. Polyacrylic Acid@zeolitic Imidazolate Framework-8 Nanoparticles with Ultrahigh Drug Loading Capability for pH-Sensitive Drug Release. Chem. Commun. 2014, 50 (8), 1000-1002.
(24) Rouquerol, J.; Rouquerol, F.; Llewellyn, P.; Maurin, G.; Sing, K. S. W. Adsorption by Powders and Porous Solids: Principles, Methodology and Applications: Second Edition; 2013.
(25) Gao, M.; Zeng, L.; Nie, J.; Ma, G. Polymer-metal-organic Framework Core-shell Framework Nanofibers via Electrospinning and Their Gas Adsorption Activities. RSC Adv. 2016, 6 (9), 7078-7085.
(26) Arjmandi, N.; Van Roy, W.; Lagae, L.; Borghs, G. Measuring the Electric Charge and Zeta Potential of Nanometer-Sized Objects Using Pyramidal-Shaped Nanopores. Anal. Chem. 2012, 84 (20), 8490-8496.
(27) Anu Prathap, M. U.; Srivastava, R.; Satpati, B. Simultaneous Detection of Guanine, Adenine, Thymine, and Cytosine at polyaniline/$MnO_2$ Modified Electrode. Electrochim. Acta 2013, 114, 285-295.
(28) Chen, T. W.; Xu, J. Y.; Sheng, Z. H.; Wang, K.; Wang, F. Bin; Liang, T. M.; Xia, X. H. Enhanced Electrocatalytic Activity of Nitrogen-Doped Graphene for the Reduction of Nitro Explosives. Electrochem. commun. 2012, 16 (1), 30-33.
(29) Chen, T. W.; Sheng, Z. H.; Wang, K.; Wang, F. Bin; Xia, X. H. Determination of Explosives Using Electrochemically Reduced Graphene. Chem.—An Asian J. 2011, 6 (5), 1210-1216.
(30) Chen, W.; Wang, Y.; Bruckner, C.; Li, C. M.; Lei, Y. Poly[meso-tetrakis(2-Thienyl)porphyrin] for the Sensitive Electrochemical Detection of Explosives. Sensors Actuators, B Chem. 2010, 147 (1), 191-197.
(31) Fierke, M. A.; Olson, E. J.; B??hlmann, P.; Stein, A. Receptor-Based Detection of 2,4-Dinitrotoluene Using

(32) Liang, Y.; Gu, L.; Liu, X.; Yang, Q.; Kajiura, H.; Li, Y.; Zhou, T.; Shi, G. Composites of Polyaniline Nanofibers and Molecularly Imprinted Polymers for Recognition of Nitroaromatic Compounds. Chem.—A Eur. J. 2011, 17 (21), 5989-5997.

(33) Lu, X.; Quan, Y.; Xue, Z.; Wu, B.; Qi, H.; Liu, D. Determination of Explosives Based on Novel Type of Sensor Using Porphyrin Functionalized Carbon Nanotubes. Colloids Surfaces B Biointerfaces 2011, 88 (1), 396-401.

(34) Nie, D.; Jiang, D.; Zhang, D.; Liang, Y.; Xue, Y.; Zhou, T.; Jin, L.; Shi, G. Two-Dimensional Molecular Imprinting Approach for the Electrochemical Detection of Trinitrotoluene. Sensors Actuators, B Chem. 2011, 156 (1), 43-49.

(35) Pesavento, M.; D'Agostino, G.; Alberti, G.; Biesuz, R.; Merli, D. Voltammetric Platform for Detection of 2,4,6-Trinitrotoluene Based on a Molecularly Imprinted Polymer. Anal. Bioanal. Chem. 2013, 405 (11), 3559-3570.

(36) Qu, Y.; Liu, Y.; Zhou, T.; Shi, G.; Jin, L. Electrochemical Sensor Prepared from Molecularly Imprinted Polymer for Recognition of 1,3-Dinitrobenzene (DNB). Chinese J. Chem. 2009, 27 (10), 2043-2048.

(37) Shi, G.; Qu, Y.; Zhai, Y.; Liu, Y.; Sun, Z.; Yang, J.; Jin, L. {MSU/PDDA}n LBL Assembled Modified Sensor for Electrochemical Detection of Ultratrace Explosive Nitroaromatic Compounds. Electrochem. commun. 2007, 9 (7), 1719-1724.

(38) Yang, R.; Wei, Y.; Yu, Y.; Gao, C.; Wang, L.; Liu, J. H.; Huang, X. J. Make It Different: The Plasma Treated Multi-Walled Carbon Nanotubes Improve Electrochemical Performances toward Nitroaromatic Compounds. Electrochim. Acta 2012, 76, 354-362.

(39) Alizadeh, T. Preparation of Magnetic TNT-Imprinted Polymer Nanoparticles and Their Accumulation onto Magnetic Carbon Paste Electrode for TNT Determination. Biosens. Bioelectron. 2014, 61, 532-540.

(40) Shi, L.; Hou, A. G.; Chen, L. Y.; Wang, Z. F. Electrochemical Sensor Prepared from Molecularly Imprinted Polymer for Recognition of TNT. Polym. Compos. 2015, 36 (7), 1280-1285.

(41) Üzer, A.; Erçağ, E.; Apak, R. Selective Colorimetric Determination of TNT Partitioned between an Alkaline Solution and a Strongly Basic Dowex 1-X8 Anion Exchanger. Forensic Sci. Int. 2008, 174 (2-3), 239-243.

(42) Cortada, C.; Vidal, L.; Canals, A. Determination of Nitroaromatic Explosives in Water Samples by Direct Ultrasound-Assisted Dispersive Liquid-Liquid Microextraction Followed by Gas Chromatography-Mass Spectrometry. Talanta 2011, 85 (5), 2546-2552.

(43) Chevallier, E.; Scorsone, E.; Girard, H. A.; Pichot, V.; Spitzer, D.; Bergonzo, P. Metalloporphyrin-Functionalised Diamond Nano-Particles as Sensitive Layer for Nitroaromatic Vapours Detection at Room-Temperature. Sensors Actuators, B Chem. 2010, 151 (1), 191-197.

(44) Jamil, A. K. M.; Izake, E. L.; Sivanesan, A.; Fredericks, P. M. Rapid Detection of TNT in Aqueous Media by Selective Label Free Surface Enhanced Raman Spectroscopy. Talanta 2015, 134, 732-738.

(45) Romolo, F. S.; Ferri, E.; Mirasoli, M.; D'Elia, M.; Ripani, L.; Peluso, G.; Risoluti, R.; Maiolini, E.; Girotti, S. Field Detection Capability of Immunochemical Assays during Criminal Investigations Involving the Use of TNT. Forensic Sci. Int. 2015, 246, 25-30.

(46) Mirasoli, M.; Buragina, A.; Dolci, L. S.; Guardigli, M.; Simoni, P.; Montoya, A.; Maiolini, E.; Girotti, S.; Roda, A. Development of a Chemiluminescence-Based Quantitative Lateral Flow Immunoassay for on-Field Detection of 2,4,6-Trinitrotoluene. Anal. Chim. Acta 2012, 721, 167-172.

(47) Wilson, R.; Clavering, C.; Hutchinson, A. Electrochemiluminescence Enzyme Immunoassays for TNT and Pentaerythritol Tetranitrate. Anal. Chem. 2003, 75 (16), 4244-4249.

(48) Goh, M. S.; Pumera, M. Graphene-Based Electrochemical Sensor for Detection of 2,4,6-Trinitrotoluene (TNT) in Seawater: The Comparison of Single-, Few-, and Multilayer Graphene Nanoribbons and Graphite Microparticles. Anal. Bioanal. Chem. 2011, 399 (1), 127-131.

(49) Xia, Y.; Song, L.; Zhu, C. Turn-on and near-Infrared Fluorescent Sensing for 2,4,6-Trinitrotoluene Based on Hybrid (Gold Nanorod)-(Quantum Dots) Assembly. Anal. Chem. 2011, 83 (4), 1401-1407.

(50) Qu, W.-G.; Deng, B.; Zhong, S.-L.; Shi, H.-Y.; Wang, S.-S.; Xu, A.-W. Plasmonic Resonance Energy Transfer-Based Nanospectroscopy for Sensitive and Selective Detection of 2,4,6-Trinitrotoluene (TNT). Chem. Commun. 2011, 47 (4), 1237-1239.

(51) Senesac, L.; Thundat, T. G. Nanosensors for Trace Explosive Detection. Materials Today. 2008, pp 28-36.

What is claimed is:

1. A method to make metal-organic frameworks (MOFs), the method comprising mixing a first aqueous solution comprising a transition metal salt with a second aqueous solution comprising imidazole or alkyl-substituted imidazole for a time and at a temperature to yield a product solution containing MOF crystals;
   wherein the first aqueous solution comprises from about 0.01 M to about 0.5 M of the transition metal salt and the second aqueous solution comprises about 1 mM to about 100 mM of the imidazole or alkyl-substituted imidazole.

2. The method of claim 1, wherein the transition metal salt in the first aqueous solution comprises a metal selected from the group consisting of scandium, titanium, vanadium, chromium, manganese, iron, cobalt, nickel, copper, and zinc, and an anion selected from the group consisting of nitrate, sulfate, acetate, and halide.

3. The method of claim 2, wherein the transition metal salt in the first aqueous solution comprises zinc nitrate.

4. The method of claim 3, wherein the second aqueous solution comprises 2-methylimidazole.

5. The method of claim 1, wherein the second aqueous solution comprises 2-methylimidazole.

6. The method of claim 1, comprising mixing the first aqueous solution and the second aqueous solution for a time of about 1 minute to about 10 minutes.

7. The method of claim 1, comprising mixing the first aqueous solution and the second aqueous solution at a temperature of about 20±5°.

8. The method of claim 1, further comprising separating the MOF crystals from the product solution.

9. The method of claim 8, comprising separating the MOF crystals from the product solution via centrifugation.

10. The method of claim 8, further comprising, after the MOF crystals are separated from the product solution, drying the MOF crystals.

11. The method of claim 8, wherein the MOF crystals are air-dried at a temperature of about 40° C. to about 100° C.

12. A composition of matter which is not ZIF-8, made by mixing a first aqueous solution comprising a transition metal salt with a second aqueous solution comprising imidazole or alkyl-substituted imidazole for a time and at a temperature to yield a product solution containing MOF crystals;
   wherein the first aqueous solution comprises from about 0.01 M to about 0.5 M of the transition metal salt and the second aqueous solution comprises about 1 mM to about 100 mM of the imidazole or alkyl-substituted imidazole.

13. The composition of matter of claim 12, wherein the transition metal salt in the first aqueous solution comprises a metal selected from the group consisting of scandium, titanium, vanadium, chromium, manganese, iron, cobalt, nickel, copper, and an anion selected from the group consisting of nitrate, sulfate, acetate, and halide.

14. The composition of matter of claim 12, wherein the second aqueous solution comprises 2-methylimidazole.

\* \* \* \* \*